(12) United States Patent
McGowan et al.

(10) Patent No.: US 11,596,530 B2
(45) Date of Patent: Mar. 7, 2023

(54) LIGHT WEIGHT, MODULAR, POWERED, TRANSFEMORAL PROSTHESIS

(71) Applicant: The Texas A&M University System, College Station, TX (US)

(72) Inventors: Daniel McGowan, Houston, TX (US); Pilwon Hur, College Station, TX (US)

(73) Assignee: The Texas A&M University System, College Station, TX (US)

( * ) Notice: Subject to any disclaimer, the term of this patent is extended or adjusted under 35 U.S.C. 154(b) by 369 days.

(21) Appl. No.: 16/769,013

(22) PCT Filed: Dec. 12, 2018

(86) PCT No.: PCT/US2018/065071
§ 371 (c)(1),
(2) Date: Jun. 2, 2020

(87) PCT Pub. No.: WO2019/118534
PCT Pub. Date: Jun. 20, 2019

(65) Prior Publication Data
US 2021/0085492 A1    Mar. 25, 2021

Related U.S. Application Data

(60) Provisional application No. 62/597,819, filed on Dec. 12, 2017.

(51) Int. Cl.
*A61F 2/64*        (2006.01)
*A61F 2/70*        (2006.01)
(Continued)

(52) U.S. Cl.
CPC .............. *A61F 2/64* (2013.01); *A61F 2/6607* (2013.01); *A61F 2/70* (2013.01);
(Continued)

(58) Field of Classification Search
CPC .. A61F 2/64; A61F 2/6607; A61F 2/70; A61F 2002/5083; A61F 2002/607;
(Continued)

(56) References Cited

U.S. PATENT DOCUMENTS 5,246,465 A     9/1993  Rincoe et al.
9,358,137 B2 *  6/2016  Bedard ...................... A61F 2/66
(Continued)

FOREIGN PATENT DOCUMENTS

CN         112603612 A  *  4/2021  ............... A61F 2/60

OTHER PUBLICATIONS

Young, Lee W., International Search Report for PCT/US2018/065071, dated Feb. 28, 2019 [2 pages].

*Primary Examiner* — Bruce E Snow
(74) *Attorney, Agent, or Firm* — Winstead PC

(57) ABSTRACT

In an embodiment, a prosthetic leg including a modular knee element coupled to a modular ankle element. The modular knee element includes a knee motor rotatable about an axis of a shaft in the knee motor. The modular ankle element includes a drive portion coupled to a surface-contacting portion via a pylon having a top and bottom end. The top end is coupled to the drive portion and the bottom end is coupled to the surface-contacting portion. The drive portion includes an ankle motor coupled to a rotary series elastic actuator (RSEA) and a first pulley coupled to the RSEA. The surface-contacting portion includes a hinge and a second pulley with a belt engaging at least a portion of at least one of the first and second pulley, and a modular foot element coupled to the bottom of the hinge.

18 Claims, 19 Drawing Sheets

(51) Int. Cl.
   *A61F 2/66* (2006.01)
   *A61F 2/50* (2006.01)
   *A61F 2/60* (2006.01)

(52) U.S. Cl.
   CPC . *A61F 2002/5083* (2013.01); *A61F 2002/607* (2013.01); *A61F 2002/6614* (2013.01); *A61F 2002/701* (2013.01); *A61F 2002/704* (2013.01)

(58) Field of Classification Search
   CPC ........ A61F 2002/6614; A61F 2002/701; A61F 2002/704
   See application file for complete search history.

(56) References Cited

U.S. PATENT DOCUMENTS

| | | | |
|---|---|---|---|
| 10,588,759 B2* | 3/2020 | Herr | A61F 2/64 |
| 10,765,537 B2* | 9/2020 | Smith | A61F 2/70 |
| 10,828,767 B2* | 11/2020 | Smith | B25J 9/148 |
| 2009/0299480 A1 | 12/2009 | Gilbert et al. | |
| 2014/0088729 A1 | 3/2014 | Herr et al. | |
| 2016/0158029 A1 | 6/2016 | Kuiken et al. | |
| 2016/0207201 A1 | 7/2016 | Herr et al. | |
| 2017/0086991 A1 | 3/2017 | Casler et al. | |

* cited by examiner

LIGHT WEIGHT, MODULAR, POWERED, TRANSFEMORAL PROSTHESIS

CROSS-REFERENCE TO RELATED APPLICATIONS

This patent application claims priority from, and incorporates by reference the entire disclosure of, U.S. Provisional Patent Application No. 62/597,819 filed on Dec. 12, 2017.

TECHNICAL FIELD

The present disclosure relates generally to transfemoral prosthetics and more particularly, but not by way of limitation, to systems and methods for a lightweight, modular, powered transfemoral prosthesis.

BACKGROUND

Amputations impact the lives of a significant portion of the world's population. Many people require some type of rehabilitation for mobility and living happy lives. In the United States, lower extremity amputations occur at a rate of approximately 185,000 people per year. It also takes up to 60% more metabolic energy compared to healthy subjects for transfemoral amputees to walk. Even though many rehabilitation and treatment options exist, no product today can mimic the full functionality of a human limb.

SUMMARY OF THE INVENTION

In an embodiment, a prosthetic leg that includes a modular knee element coupled to a modular ankle element. The modular knee element includes a knee motor, where the modular knee element is rotatable about an axis of a shaft in the knee motor. The modular ankle element includes a drive portion coupled to a surface-contacting portion via a pylon that includes a top end and a bottom end, where the top end of the pylon is coupled to the drive portion of the modular ankle element and the bottom end of the pylon is coupled to the surface-contacting portion of the modular ankle element. The drive portion of the modular ankle element includes an ankle motor coupled to a rotary series elastic actuator (RSEA) and a first pulley coupled to the RSEA. The surface-contacting portion of the modular ankle element includes a shaft and flange engaged in a hinge rotatable about an axis of the shaft and flange and a second pulley coupled to the shaft and flange. Further, the prosthetic leg includes a belt engaging at least a portion of at least one of the first pulley and the second pulley, and a modular foot element coupled to the bottom of the hinge.

In another embodiment, a control system for a prosthetic leg, where the control system includes a control unit, a knee motor operatively coupled to the control unit, an ankle motor operatively coupled to the control unit, a first sensor disposed proximate a knee joint of the prosthetic leg and operatively coupled to the control unit, the first sensor being configured to measure angular displacement of a thigh of a user in a sagittal plane about an axis of rotation through a hip joint of the user, a second sensor disposed proximate a knee motor of the prosthetic leg and operatively coupled to the control unit, the second sensor being configured to measure angular displacement of a knee joint of the user. The control system for the prosthetic leg further includes a third sensor disposed proximate a foot element of the prosthetic leg and operatively coupled to the control unit, the third sensor being configured to measure contact force between the foot element and a surface, where the control unit selectively actuates at least one of the knee motor and the ankle motor responsive to signals received from at least one of the first sensor, the second sensor, and the third sensor.

In a further embodiment, a powered prosthetic leg that includes a modular knee element coupled to a modular ankle element. The modular knee element includes a bracket operable to connect to a residual limb and a knee motor coupled to a knee harmonic drive, where the modular knee element is rotatable about an axis of a shaft in the knee motor. The modular ankle element includes a drive portion coupled to a surface-contacting portion via an adjustable pylon including a top end and a bottom end, where the top end of the adjustable pylon is coupled to the drive portion of the modular ankle element and the bottom end of the adjustable pylon is coupled to the surface-contacting portion of the modular ankle element. The drive portion of the modular ankle element includes an ankle motor coupled to an ankle harmonic drive a rotary series elastic actuator (RSEA) coupled to the ankle harmonic drive, and a first pulley coupled to the RSEA. The surface-contacting portion of the modular ankle element includes a shaft and flange engaged in a hinge rotatable about an axis of the shaft and flange, a spring element connected above the hinge and below the hinge, and a second pulley coupled to the shaft and flange. The powered prosthetic leg further includes a belt engaging at least a portion of at least one of the first pulley and the second pulley and a modular foot element coupled to the bottom of the hinge.

BRIEF DESCRIPTION OF THE DRAWINGS

A more complete understanding of the subject matter of the present disclosure may be obtained by reference to the following Detailed Description when taken in conjunction with the accompanying Drawings wherein.

DETAILED DESCRIPTION

Figure 1A:
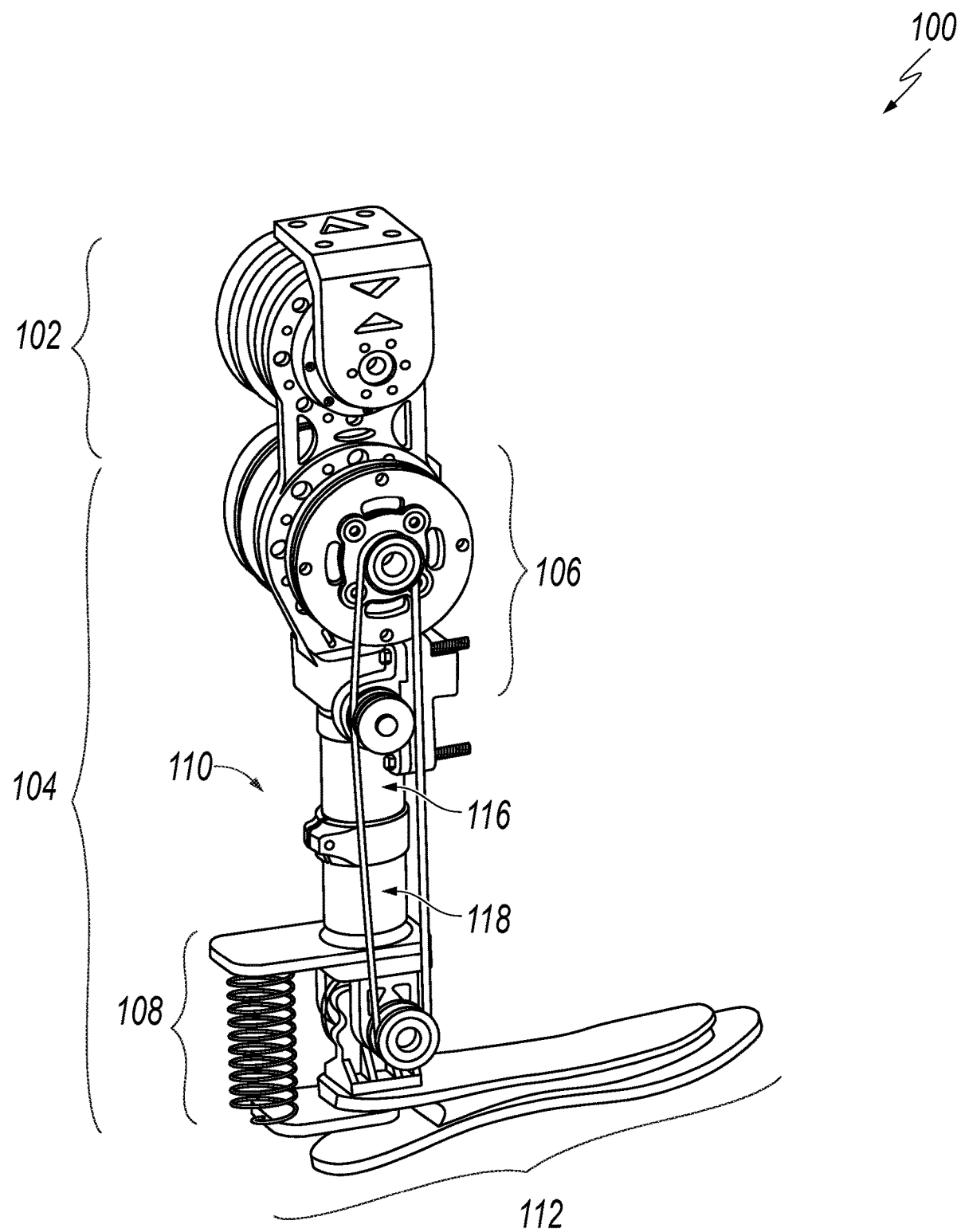
FIG. 1A illustrates a perspective view of a powered prosthetic leg according to an embodiment of the present disclosure.

It is to be understood that the following disclosure provides many different embodiments, or examples, for implementing different features of various embodiments. Specific examples of components and arrangements are described below to simplify the disclosure. These are, of course, merely examples and are not intended to be limiting. The section headings used herein are for organizational purposes and are not to be construed as limiting the subject matter described.

Powered prosthetics have potential to close the gap between passive prosthetics and healthy limbs. Currently, only a few powered ankles and powered knees are available to users. However, these devices have drawbacks that include cost, lack of functionality, mass, and bulky designs. Mass and bulk, for example, significantly increase a user's energy expenditure and can negate the benefits of a powered device. For proper imitation of able-bodied limbs, prosthetic devices should be able to mimic functionality, speeds, and torques of healthy humans with minimal weight and volume. To identify these requirements, kinematic and kinetic joint data are calculated using, for example, inverse dynamics. Joint torque and speed can be estimated based on the weight of the user using this method. The prosthetic designs presented herein allows for proper ankle joint torque and knee joint torque profiles and energy profiles to meet proper power and work expectations for lower limb prosthetics.

High torque requirements contribute to the high weight of powered lower limb prosthetics. In order to generate the required power, heavy motors with large gearing systems could be employed. However, meeting the power requirements solely through motors and gearing is not viable due to the mass and resulting footprint of motors that are capable of generating such a torque. Alternatively, other methods could be utilized to produce and store the required power. Rather than removing the motors and returning to fully passive devices, mixing both passive and powered components reduces the required power of the motors, which will allow less bulky and lighter-weight prosthetics, reducing the energy expenditure of the user. Elastic energy storage and return has the potential to replicate the profiles of healthy limbs. Successful use of elastic energy storage can be achieved through the use of a Linear Series Elastic Actuator (LSEA). The use of an LSEA for a robotic tendon shows great potential at reducing energy requirements to power a prosthetic. This concept includes a linear actuator and spring in series which provide a torque to the ankle by pushing down on a moment arm secured to the ankle joint. The LSEA can reduce peak power requirements for the ankle. Due to its advantages, LSEAs can be employed to enhanced energy consumption on the prosthetics, and can include, for example, a clutchable knee device or a spring on the foot which gathers energy from an ankle dorsiflexion.

Another mechanism that can be employed in prosthetics is a Rotary Series Elastic Actuator (RSEA). RSEA devices can be used for torque control, shock tolerance, energy storage, and to reduce stiffness between the device and the user. An RSEA is similar to an LSEA in that it consists of a deflecting spring in series with an actuator. In contrast, however, the spring of an RSEA is designed as a torsion spring machined from a flat disk. Rather than relying on linear motion and requiring a moment arm to generate the joint torque, the RSEA spring is in line with the motor shaft keeping the energy rotational. On prosthetics, these devices are normally used for improved torque control rather than reducing power requirements.

Functional powered lower limb prosthetics today aim at mimicking able-bodied limbs. There is a growing trend of taking advantage of springs (e.g., an LSEA) as a means to reduce energy requirements. Some powered lower limb prosthetic devices are able to closely follow the joint torque and power curves of an ankle during the walking cycle (i.e., gait cycle). These devices use an LSEA, but are undesirably bulky and heavy. Other devices use more simplified approaches and include some motors and gearing on a single frame. Such devices can be lighter weight due to fewer components; however, due to the high power and torque requirements, such devices are usually only capable of flatfoot walking, which is unnatural and undesirable as flatfoot walking leads to increased energy expenditure.

Prosthetics today fail to come close to mimicking the full functionality of healthy limbs. Powered devices have potential to provide missing functionality, but quickly become unrealistic with the required complexity and added mass of powered components. This ultimately increases the energy expenditure of the user rather than decrease it over passive devices. As such, the present disclosure seeks to provide the functionality of healthy limbs while focusing on reducing mass and volume, and maintain gait symmetry.

The present disclosure relates generally to reducing the energy expenditure of the user and accommodating a larger range of users. Mass is a design factor in parts selection, as motors and gearing make up the heaviest components of the device. The motors and gearing systems have thus been selected based on an optimization-based approach. Structural components are the second heaviest components and as such, material volume reduction is another factor considered. To be useful for a multitude of users, modularity is also a factor to consider. Unlike existing powered prosthetics, the devices of the present disclosure can be adjustable for users of different heights or for use on either leg. The modularity of such components also allows easy adjustment for the needs of different users. Furthermore, modularity also allows specific components to be upgraded in the future without the need of redesigning, or updating, the entire device. For example, a flexible off-the-shelf foot can be utilized, but can be upgraded to a custom foot later. Keeping modularity in mind while designing components helps reduce compatibility problems by allowing adjustments on the device without expensive intervention by engineers or doctors. The prosthetic devices disclosed herein can also to be used in a research lab and allow for creating a product capable of interchanging components for various purposes that can vastly increases the potential of research in the lab.

The prosthetic devices of the present disclosure can allow for heavy components such as, for example, motors and gearing, and electronic components to be placed close together and as close to the residual limb as possible. Placing these components near the residual limb aids in modularity as each part of the prosthetic devices can be designed in sub-sections and interchanged. This also reduces strain on the user, as the heavy components will create less of a moment arm during a leg swing if they are closer to the residual limb. Furthermore, high mass can cause increased energy expenditure of the user, and as such, components can be selected in an attempt to minimize the weight of, for example, motors and gearing, and structural components. Moreover, presented herein are elastic components, providing for lighter weight means of storing and providing some of the power during walking, are discussed.

Figure 1B:
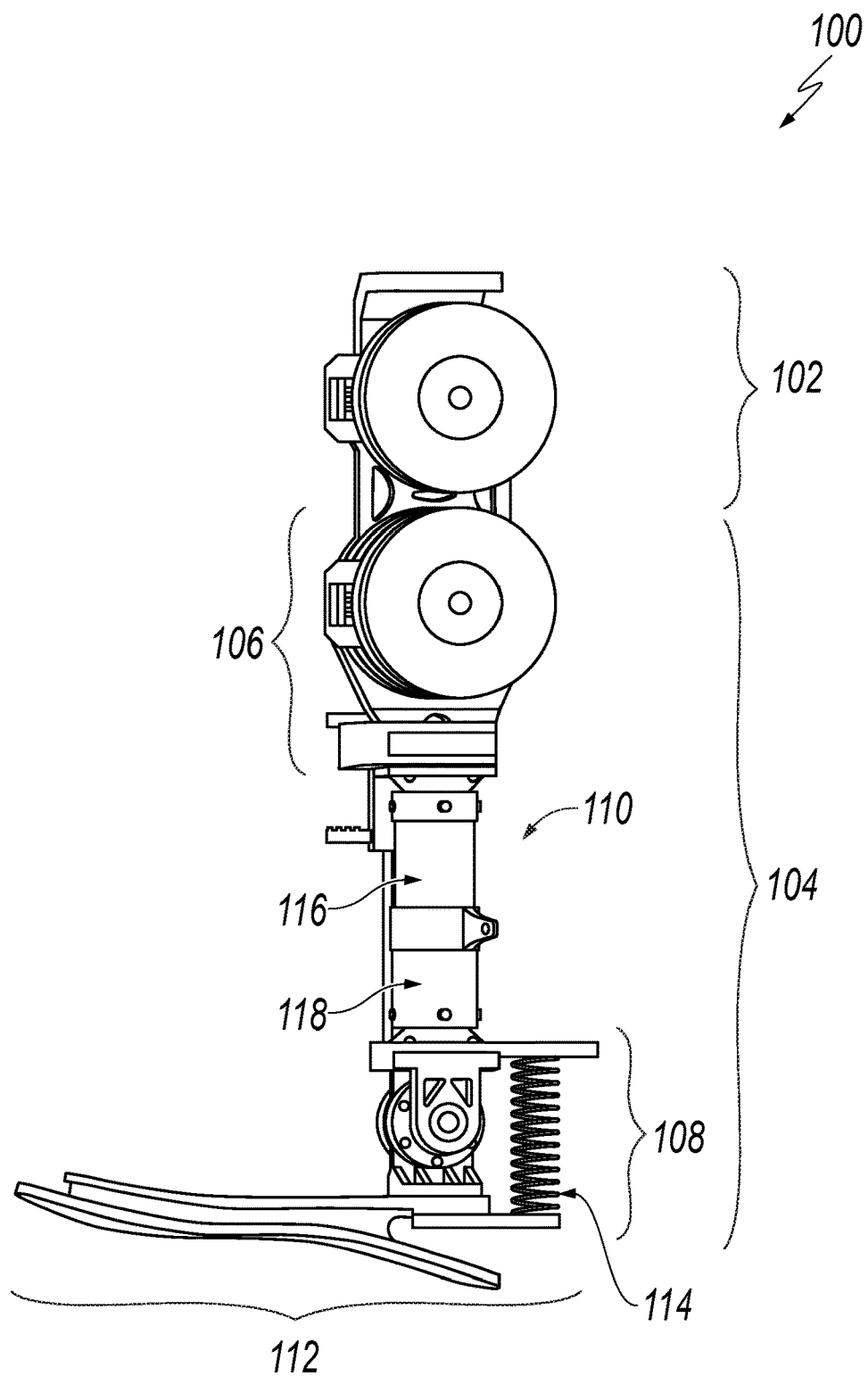
FIG. 1B illustrates another perspective view of the powered prosthetic leg of FIG. 1A.

FIG. 1A and FIG. 1B illustrate perspective views of a powered prosthetic leg 100 according to an embodiment of the present disclosure. The powered prosthetic leg 100 of FIG. 1A and FIG. 1B includes a modular knee element 102 coupled to a modular ankle element 104. The modular ankle element 104 includes a drive portion 106 coupled to a surface-contacting portion 108 via an adjustable pylon 110. In some embodiments, the adjustable pylon 110 can be constructed of, for example, plastics, metals, metal-alloys, carbon-fiber composites, and combinations of the same and like. In some embodiments, the adjustable pylon 110 can be cylindrical telescopic tubes or square telescopic components. In various embodiments, the adjustable pylon 110 may include of two parts, a first pylon-section 116 and a second pylon-section 118 with an internal and/or external setscrew to allow for height adjustments and securement of the first pylon-section 116 and the second pylon-section 118 with respect to each other. In various embodiments, vertical adjustment of the pylon 110 facilitates, for example, use of the powered prosthetic leg 100 with users of a variety of heights.

As shown in FIG. 1A and FIG. 1B, a modular foot element 112 is coupled to the surface-contacting portion 108 of the modular ankle element 104. In various embodiments, the surface-contacting portion 108 can include a spring element 114 as shown in FIG. 1A and FIG. 1B. In other embodiments, the surface-contacting portion 108 may omit the spring element 114 shown in FIG. 1A and FIG. 1B, as will be discussed in further detail below. The powered prosthetic leg 100 can be operable to connect to a residual limb of an individual or machine to mimic the functionality of a human leg. As will be discussed in more detail below, the powered prosthetic leg 100 is segmented into various modules and portions. In this manner, various modules such as, for example, the modular foot element 112 can be replaced and/or customized without interaction with the other modules, such as, for example, the modular knee element 102 and the modular ankle element 104. Thus, the modular knee element 102, the modular ankle element 104, and the modular foot element 112 may be selectively interchanged to facilitate use of the powered prosthetic leg 100 in a variety of applications.

Figure 2:
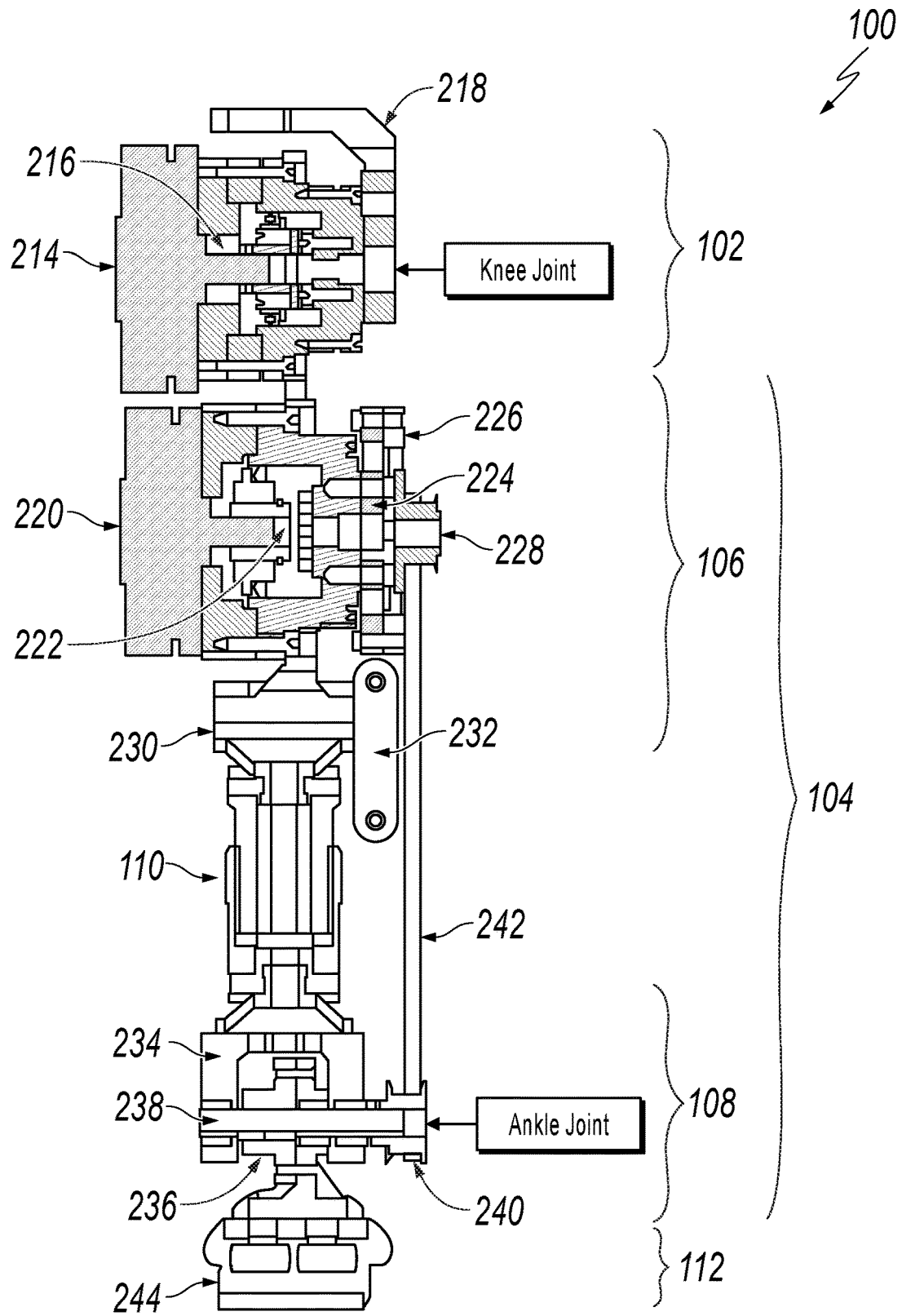
FIG. 2 illustrates a cross sectional view of the powered prosthetic leg according to an embodiment of the present disclosure.

FIG. 2 illustrates a cross sectional view of the powered prosthetic leg 100 according to an embodiment of the present disclosure. The powered prosthetic leg 100 of FIG. 2 includes the modular knee element 102 coupled to the modular ankle element 104. The modular ankle element 104 includes the drive portion 106 coupled to the surface-contacting portion 108 via the adjustable pylon 110. As shown in FIG. 2, the modular foot element 112 is coupled to the surface-contacting portion 108 of the modular ankle element 104. The modular knee element 102 includes a knee motor 214 coupled to a knee harmonic drive 216 that forms a "knee joint" of the powered prosthetic leg 100. In various embodiments, the knee motor 214 can be an alternating current (AC) or direct current (DC) motor. In some embodiments, the knee motor 214 can be a brushless DC motor. In some embodiments, the knee motor 214 can be powered via batteries or other suitable portable power source. The modular knee element 102 can further include a bracket 218 operable to connect to a residual limb. During operation, the knee motor 214 is configured to apply a torque to the knee joint sufficient to cause flexion and extension of the knee joint in the sagittal plane (i.e., the anterior-posterior plane) of the user.

In some embodiments, the bracket 218 can be constructed of, for example, plastics, metals, metal-alloys, carbon-fiber composites, and combinations of the same and like. In various embodiments, the bracket 218 can attach to the residual limb by anchoring the bracket 218 to a component operable to receive the bracket 218. The bracket 218 can be mounted, for example, via screws, setscrews, lock pins, latches, and/or nuts and bolts to a component operable to receive the bracket 218. In various embodiments, the bracket 218 can be utilized to connect the powered prosthetic leg 100 to a human or a machine. The drive portion 106 of the modular ankle element 104 includes an ankle motor 220 coupled to an ankle harmonic drive 222 that is in turn coupled to a rotary series elastic actuator (RSEA) 224. In various embodiments, the ankle motor 220 can be an AC or DC motor. In some embodiments, the ankle motor 220 can be a brushless DC motor. In some embodiments, the ankle motor 220 can be powered via batteries or other suitable portable power source. A connecting disk 226 has a first pulley 228 coupled thereon, and the connecting disk 226 is coupled to the RSEA 224. In some embodiments, the connecting disk 226 can be constructed of, for example, plastics, metals, metal-alloys, aluminum, carbon-fiber composites, steel, steel-alloys, and combinations of the same and like. In some embodiments, the knee harmonic drive 216 and the ankle harmonic drive 222 can be, for example, a strain wave gear. In various embodiments, the knee harmonic drive 216 and the ankle harmonic drive 222 can provide large gearing ratios in small profiles. In some embodiments, the RSEA 224 can be omitted and a rigid ankle joint mount can be coupled to the ankle harmonic drive 222, thereby removing the connecting disk 226 and the first pulley 228 can then be coupled to the rigid ankle joint mount.

In various embodiments, the RSEA 224 can be constructed of, for example, plastics, metals, metal-alloys, aluminum, carbon-fiber composites, steel, steel-alloys, and combinations of the same and like. In some embodiments, the RSEA 224 can deflect about 5 degrees without yielding to approximately 172 Nm. In various embodiments, the RSEA 224 can be constructed of, for example, Maraging Steel 300. As shown in FIG. 2, coupled at a lower end of the drive portion 106 of the modular ankle element 104 via a tensioner-mounting bracket 230 is a belt tensioner 232. In some embodiments, the tensioner-mounting bracket 230 and the belt tensioner 232 can be constructed of, for example, plastics, metals, metal-alloys, aluminum, carbon-fiber composites, steel, steel-alloys, and combinations of the same and like. In various embodiments, the tensioner-mounting bracket 230 can wrap around a bottom portion of the drive portion 106 to reduce required mounting space. In some embodiments, the belt tensioner 232 can be a pillow block and a custom pulley operable to move away from the tensioner-mounting bracket 230, and can, for example, be locked in place with, for example, screws and/or setscrews. In some embodiments, using screws to lock a pillow block allows for fine-tuning of the belt tensioner 232.

The adjustable pylon 110 is coupled to a top end of the surface-contacting portion 108 of the drive portion 106 thereby forming the modular ankle element 104. The surface-contacting portion 108 includes an upper hinge portion 234 rotatably coupled to a lower hinge portion 236 via a shaft 238 disposed through an opening of the upper hinge portion 234 and an aligned opening of the lower hinge portion 236 thereby creating a hinge that forms an "ankle joint" of the powered prosthetic leg 100. In some embodiments, the upper hinge portion 234 and the lower hinge portion 236 can be constructed of, for example, plastics, metals, metal-alloys, aluminum, carbon-fiber composites, steel, steel-alloys, and combinations of the same and like. In various embodiments, the shaft 238 can be constructed of, for example, plastics, metals, metal-alloys, aluminum, carbon-fiber composites, steel, steel-alloys, and combinations of the same and like. As shown in FIG. 2, a second pulley 240 is coupled to the shaft 238, and a belt 242 at least partially engages the first pulley 228 and the second pulley 240. In particular embodiments, the belt 242 at least partially engages a tension pulley (not shown) coupled to the belt tensioner 232. The lower hinge portion 236 of the surface-contacting portion 108 is coupled to the modular foot element 112, which includes a flexible foot 244.

In some embodiments, the belt 242 can be, for example, an elastic belt, a chain, a flat belt, a rope belt, such as a wire belt, a V belt, a round belt, a single groove belt, a multi-groove belt, a ribbed belt, a film belt, a toothed, notched, cogged, or other synchronous belt, and combinations of the same and like. In various embodiments, the belt 242 can be constructed of, for example, elastomers, such as polymer materials with high elastic nature that can include, but are not limited to, natural rubber, synthetic rubber, nitrile rubber, silicone rubber, urethane rubbers, chloroprene rubber, poly ethylene-vinyl acetate, and combinations of the same and like. During operation, the ankle motor 220 transmits torque to the ankle joint via the first pulley 228, the belt 242, and the second pulley 240 sufficient to cause flexion and extension of the modular foot element 112 in a sagittal plane (i.e., an anterior-posterior plane) of the user.

In various embodiments, the flexible foot 244 can be custom designed for walking, running, sporting activities, and the like. In some embodiments, the flexible foot 244 can be waterproof. In some embodiments, the flexible foot 244 can be constructed of, for example, plastics, metals, metal-alloys, aluminum, carbon-fiber composites, steel, steel-alloys, and combinations of the same and like. In some embodiments, elastic elements, such as springs, can be added between and upper foot portion and a lower foot portion at an end opposite the lower hinge portion 236 to act as "toes" on the flexible foot 244. For example, the upper foot portion and the lower foot portion can extend outward and form the shape of a foot including separate extensions for each toe. Continuing this example, one or more toes formed by this configuration can have an elastic element between the upper foot portion and the lower foot portion of the flexible foot 244.

In some embodiments, the modular knee element 102 can further include sensors mounted on or inside various components of the modular knee element 102, for example, the sensors can be in or on the knee motor 214, the knee harmonic drive 216, or mounted on a sensor-bracket attached to the modular knee element 102. In these embodiments, the sensors can be encoders, inertial measurement unit sensors, force sensors, or other types of sensors that can monitor input/output information relating to angles between the powered prosthetic leg 100 and, for example, a residual limb connected via the bracket 218, or relative location/orientation of the powered prosthetic leg 100. In various embodiments, at least one first sensor is configured to measure angular displacement of the user's thigh in the sagittal plane about an axis of rotation extending through the user's hip joint in the coronal plane.

In some embodiments, the sensors can measure specific forces or angular rates, and can use a combination of accelerometers and gyroscopes. In various embodiments, the modular ankle element 104 can further include sensors mounted on or inside various components of the modular ankle element 104, for example, the sensors can be in or on the ankle motor 220, the ankle harmonic drive 222, or mounted on a sensor-bracket attached to the modular ankle element 104. In these embodiments, the sensors can be encoders, inertial measurement unit sensors, force sensors, or other types of sensors that can monitor input/output information relating to angles between the powered prosthetic leg 100 and, for example, the residual limb connected via the bracket 218 or relative location/orientation of the powered prosthetic leg 100. In some embodiments, the sensors can measure specific forces or angular rates, and can use a combination of accelerometers and gyroscopes. In some embodiments, the modular foot element 112 can further include sensors to measure force at a bottom end of the modular foot element 112. In various embodiments, the sensors can measure foot-contact reaction forces. In various embodiments, at least one second sensor is configured to measure angular displacement of the knee joint in the sagittal plane (i.e., flexion and extension of the knee joint). At least one third sensor is configured to measure contact force between the modular foot element 112 and a surface.

Figure 3B:
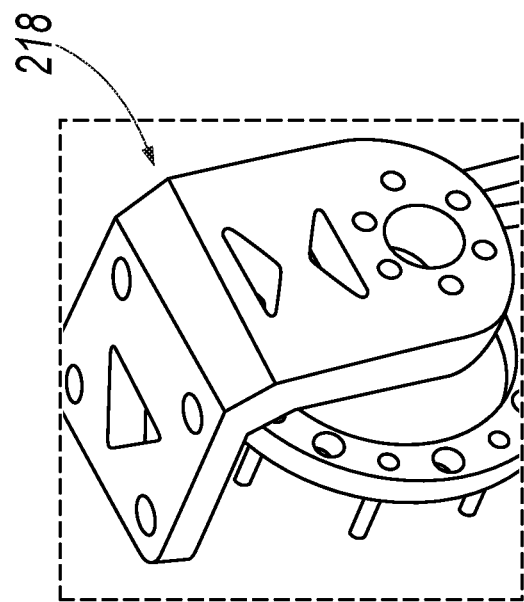
FIG. 3B illustrates an enlarged view of a bracket operable to connect to a residual limb.
Figure 3A:
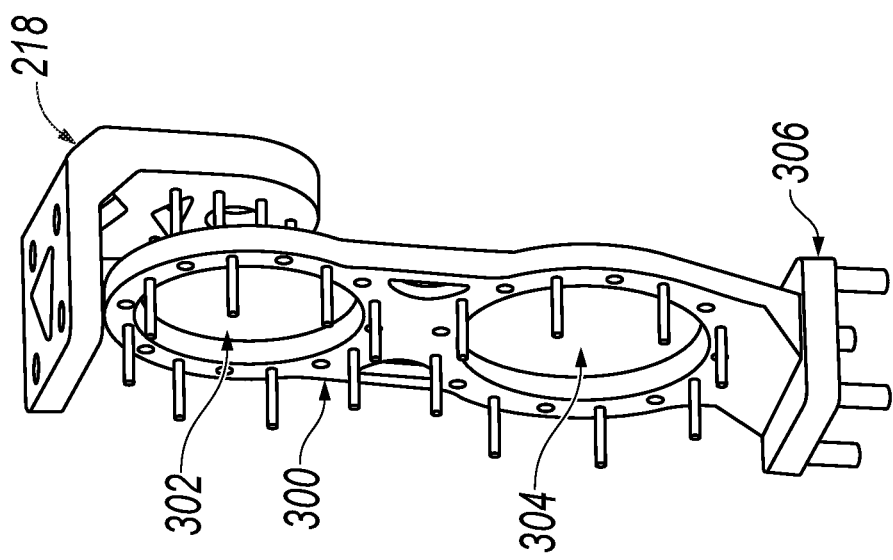
FIG. 3A illustrates an upper structural frame of the powered prosthetic leg.

FIG. 3A illustrates an upper structural frame 300 of the powered prosthetic leg 100. The upper structural frame 300 houses the modular knee element 102 and the drive portion 106 of the modular ankle element 104. In some embodiments, the upper structural frame 300 can be constructed of, for example, plastics, metals, metal-alloys, aluminum, carbon-fiber composites, steel, steel-alloys, and combinations of the same and like. The upper structural frame 300 includes an upper opening 302 to receive the modular knee element 102 and a lower opening 304 to receive the drive portion 106 of the modular ankle element 104. In various embodiments, the upper structural frame 300 can include, for example, pins, screws, setscrews, nuts and bolts, clasps, clamps, and the like, to secure the modular knee element 102 and the drive portion 106 into the upper opening 302 and the lower opening 304, respectively. The upper structural frame 300 also includes a lower coupling 306 that can couple to the adjustable pylon 110 or the tensioner-mounting bracket 230. Also shown in FIG. 3A is the bracket 218 operable to connect to the residual limb. FIG. 3B illustrates an enlarged view of the bracket 218 operable to connect to the residual limb.

Figure 4:
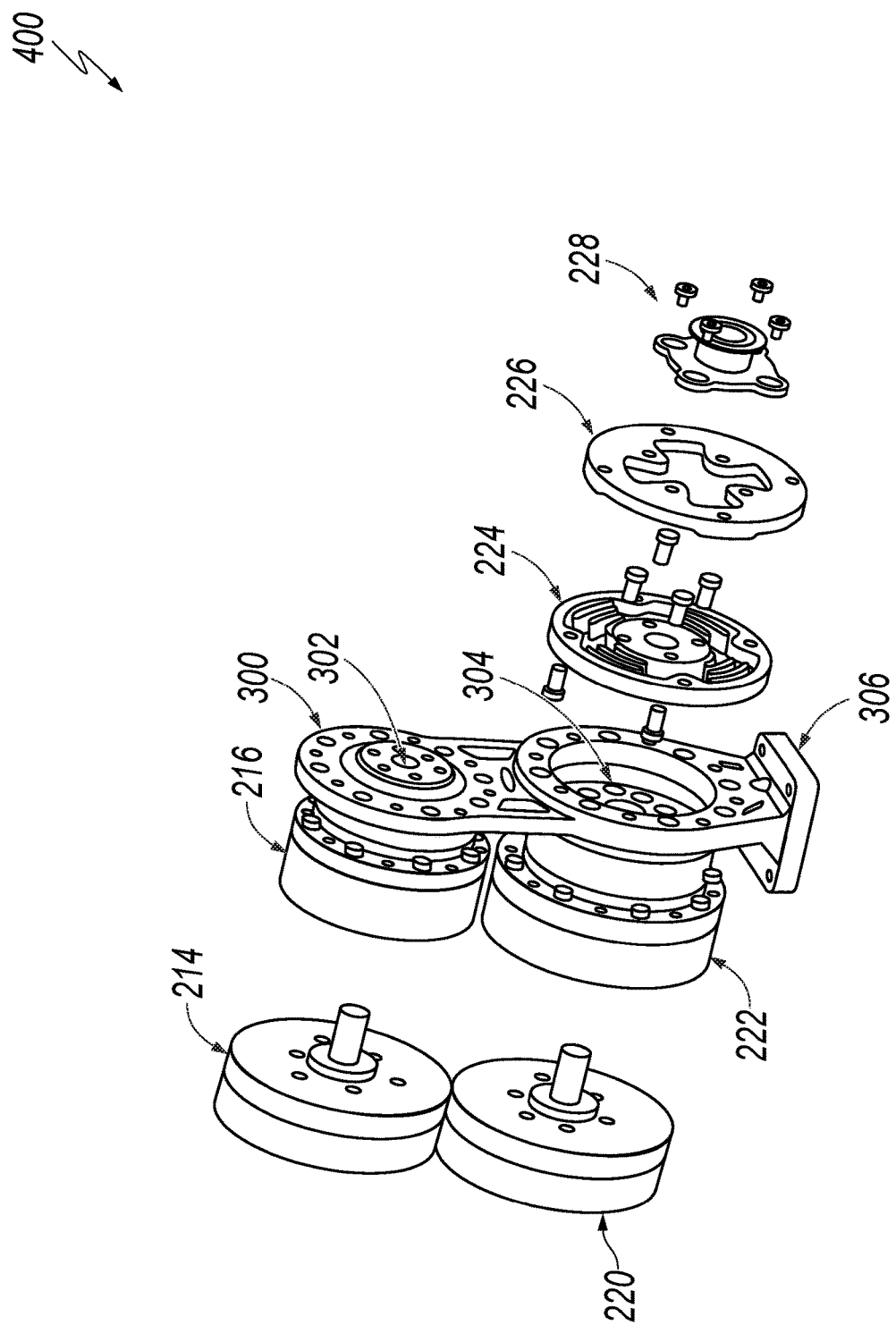
FIG. 4 illustrates an exploded view of the upper structural frame housing a modular knee element and a drive portion of a modular ankle element.

FIG. 4 illustrates an exploded view of the upper structural frame 300 housing the modular knee element 102 and the drive portion 106 of the modular ankle element 104. In some embodiments, the upper structural frame 300 and/or components coupled to the upper structural frame 300 can include various sensors as discussed with respect to FIG. 2. The upper structural frame 300 includes the upper opening 302, the lower opening 304, and the lower coupling 306 that can couple to, for example, the adjustable pylon 110 or the tensioner-mounting bracket 230. The upper opening 302 is operable to house and couple to the knee harmonic drive 216 that is in turn coupled to the knee motor 214. The lower opening 304 is operable to house and couple to the ankle harmonic drive 222 and the ankle motor 220. The RSEA 224 is coupled the ankle harmonic drive 222 opposite the ankle motor 220. The connecting disk 226 is coupled to the RSEA 224 opposite the ankle harmonic drive 222, which in turn is coupled to the first pulley 228 opposite the RSEA 224. In some embodiments, the first pulley 228 can have a contacting surface that is operable engage at least partial contact with the belt 242.

Figure 5:
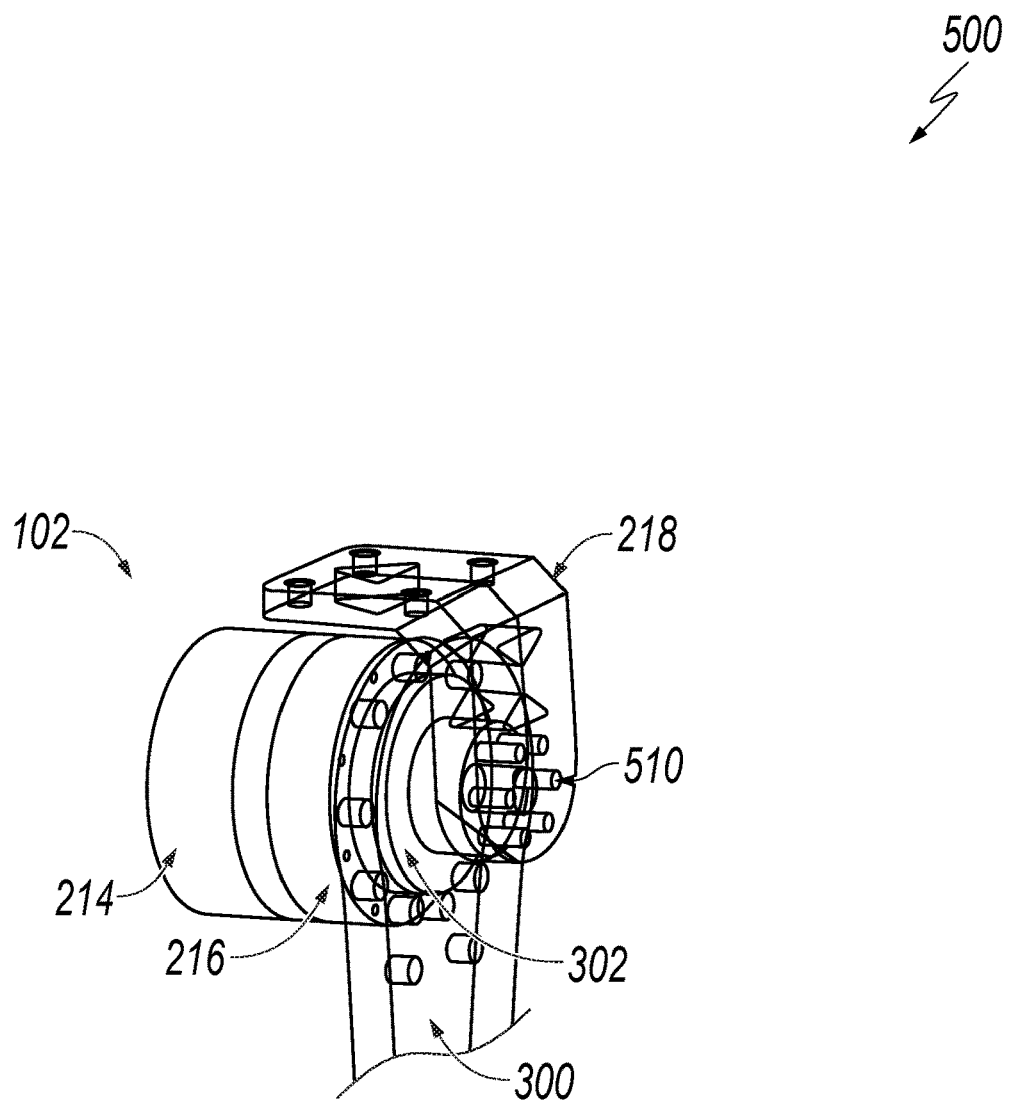
FIG. 5 illustrates the modular knee element according to an embodiment of the present disclosure.

FIG. 5 illustrates the modular knee element 102 according to an embodiment of the present disclosure. As shown in FIG. 5, the modular knee element 102 includes the knee motor 214 coupled to the knee harmonic drive 216. The knee harmonic drive 216 passes through the upper opening 302 of the upper structural frame 300 and couples to the bracket 218 operable to connect to the residual limb. The bracket 218 is coupled to the knee harmonic drive 216 via bracket-securing devices 510. In some embodiments, the bracket-securing devices 510 can be, for example, screws, pins, setscrews, bolts, clasps, clamps, and combinations of the same and like. In some embodiments, the modular knee element 102 can further include sensors mounted on or inside various components of the modular knee element 102, for example, the sensors can be in or on the knee motor 214, the knee harmonic drive 216, or mounted on a sensor-bracket, discussed in further detail below, coupled to the modular knee element 102. In these embodiments, the sensors can be encoders, inertial measurement unit sensors, force sensors, or other types of sensors that can monitor input/output information relating to angles between the powered prosthetic leg 100 and, for example, the residual limb connected via the bracket 218 or relative location/orientation of the powered prosthetic leg 100. In some embodiments, the sensors can measure specific forces or angular rates, and can use a combination of accelerometers and gyroscopes, similar to those described with respect to FIG. 2. In various embodiments, at least one first sensor is configured to measure angular displacement of the user's thigh in the sagittal plane about an axis of rotation extending through the user's hip joint in the coronal plane.

Figure 6:
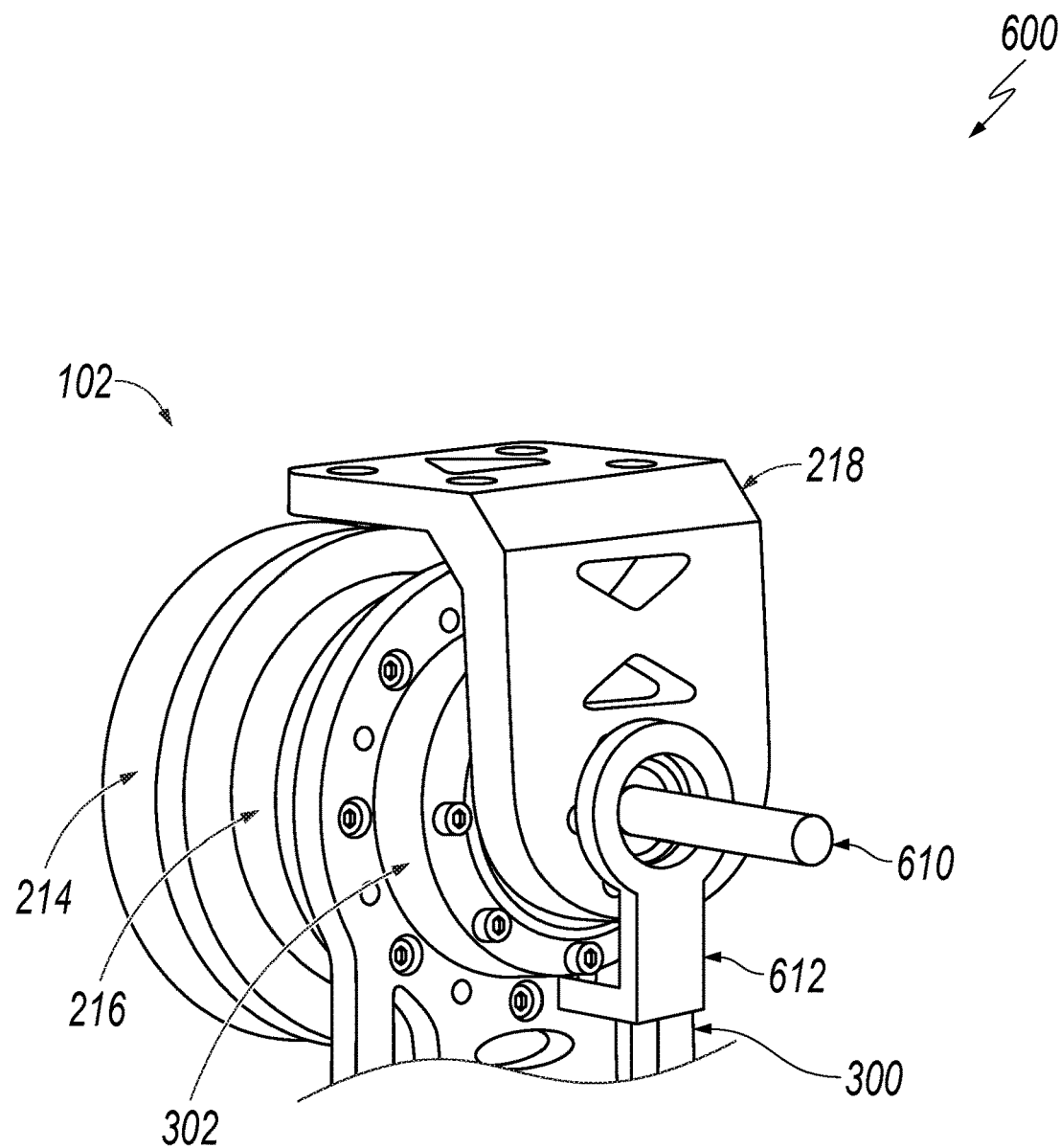
FIG. 6 illustrates the modular knee element coupled to the bracket operable to connect to the residual limb, and optionally including a sensor housed on a sensor-mounting bracket 612.

FIG. 6 illustrates the modular knee element 102 coupled to the bracket 218 operable to connect to the residual limb, and optionally including a sensor 610 housed on a sensor-mounting bracket 612. The bracket 218 is coupled to the knee harmonic drive 216 that passes through the upper opening 302 of the upper structural frame 300. The knee motor 214 is coupled to the knee harmonic drive opposite the bracket 218. The upper structural frame 300 has coupled thereon the sensor-bracket 612 housing the sensor 610. In some embodiments, the modular knee element 102 can omit the sensor-bracket 612 and the sensor 610. In various embodiments, the sensor 610 can be assembled on and/or in components of the modular knee element 102. In some embodiments, the sensor 610 can be an encoder, inertial measurement unit sensor, force sensors, or other types of sensors that can monitor input/output information relating to angles between the powered prosthetic leg 100 and, for example, the residual limb connected via the bracket 218 or relative location/orientation of the powered prosthetic leg 100. In some embodiments, the sensor 610 can measure specific forces or angular rates, and can use a combination of accelerometers and gyroscopes. In some embodiments, the sensor-bracket 612 can be constructed of, for example, plastics, metals, metal-alloys, carbon-fiber composites, and combinations of the same and like. In various embodiments, the sensors can measure foot-contact reaction forces.

Figure 7A:
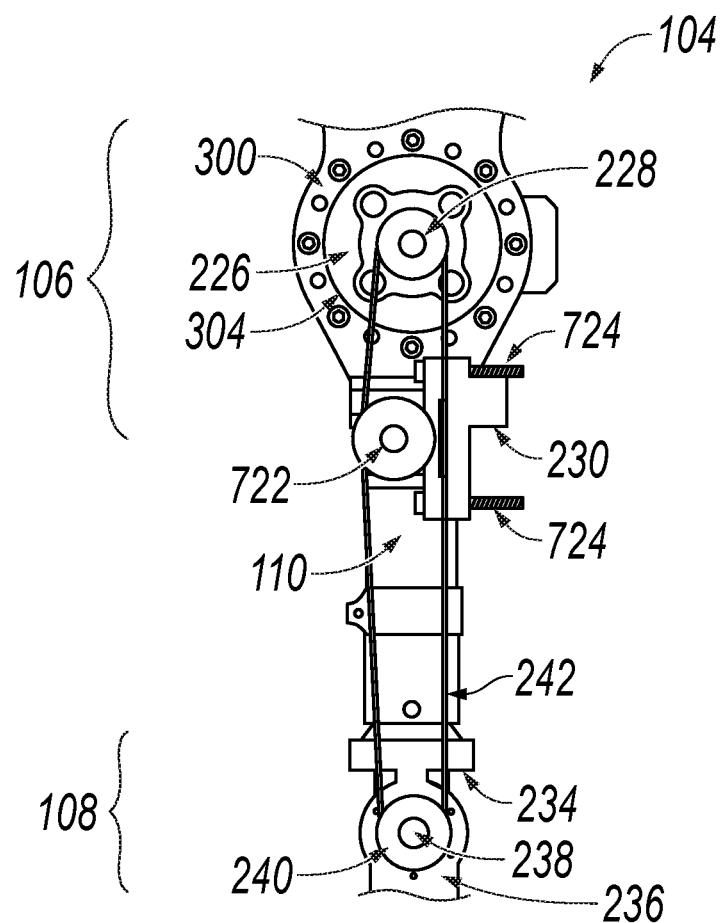
FIG. 7A illustrates the modular ankle element according to an embodiment of the present disclosure.

FIG. 7A illustrates the modular ankle element 104 according to an embodiment of the present disclosure. The modular ankle element 104 includes the drive portion 106 and the surface-contacting portion 108 coupled together via the adjustable pylon 110. As shown in FIG. 7A, the connecting disk 226 is coupled to the RSEA 224 (not shown) that is in turn coupled to the ankle harmonic drive 222 (not shown) passing through the lower opening 304 of the upper structural frame 300. The first pulley 228 is coupled to the connecting disk 226 and is in partial engagement with the belt 242. The upper structural frame 300 is coupled to a top portion of the adjustable pylon 110, having a tensioner-mounting bracket 230 coupled to the modular ankle element 104 between the upper structural frame 300 and the adjustable pylon 110. In various embodiments, the first pulley 228 can have a contacting surface that is operable to make at least partial contact with the belt 242.

In various embodiments, the modular ankle element 104 can further include sensors mounted on or inside various components of the modular ankle element 104 or mounted on a sensor-bracket, for example, a sensor-bracket substantially similar to the sensor-bracket 612 of FIG. 6, attached to the modular ankle element 104. In these embodiments, the sensors can be encoders, inertial measurement unit sensors, force sensors, or other types of sensors that can monitor input/output information relating to angles between the powered prosthetic leg 100 and, for example, the residual limb connected via the bracket 218, or relative location/orientation of the powered prosthetic leg 100. In some embodiments, the sensors can measure specific forces or angular rates, and can use a combination of accelerometers and gyroscopes, and can be substantially similar to those described with respect to FIG. 2. In various embodiments, at least one second sensor is configured to measure angular displacement of the knee joint in the sagittal plane (i.e., flexion and extension of the knee joint). At least one third sensor is configured to measure contact force between the modular foot element 112 and the surface. As will be discussed in further detail below, in some embodiments, multiple sensors can be coupled to and/or imbedded in the modular foot element 112.

Figure 7B:
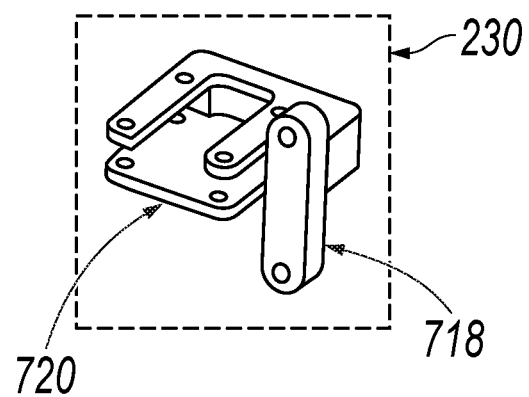
FIG. 7B illustrates an enlarged view of a tensioner-mounting bracket of FIG. 7A.

FIG. 7B illustrates an enlarged view of the tensioner-mounting bracket 230 of FIG. 7A. As shown in FIG. 7B, the tensioner-mounting bracket 230 includes a first piece 718 and a second piece 720 operable to extend outwardly from each other. In some embodiments, the first piece 718 and the second piece 720 of the tensioner-mounting bracket 230 can be composed of plastics, metals, metal-alloys, aluminum, carbon-fiber composites, steel, steel-alloys, and combinations of the same and like. As shown in FIG. 7A, the tensioner-mounting bracket 230 includes a tension pulley 722 in partial engagement with the belt 242 coupled thereon. In some embodiments, the tension pulley 722 can have a contacting surface that is operable to make at least partial contact with the belt 242.

The tension pulley 722 can be moved outwardly and/or inwardly to increase and/or decrease tension on the belt 242 by extending and/or retracting the first piece 718 and the second piece 720 of the tensioner-mounting bracket 230 and locking the first piece 718 and the second piece 720 in place with tensioner-locking devices 724. The tensioner-locking devices 724 can be, for example, screws, pins, setscrews, bolts, or combinations of the same and like. In various embodiments, the tensioner-mounting bracket 230 can wrap around a bottom portion of the drive portion 106 to reduce required mounting space. In some embodiments, the first piece 718 or the second piece 720 can be a pillow block and a custom pulley operable to move away from the tensioner-mounting bracket 230, and can, for example, be locked in place with screws and/or setscrews. In some embodiments, using screws to lock a pillow block allows for fine-tuning of tension.

Figure 7C:
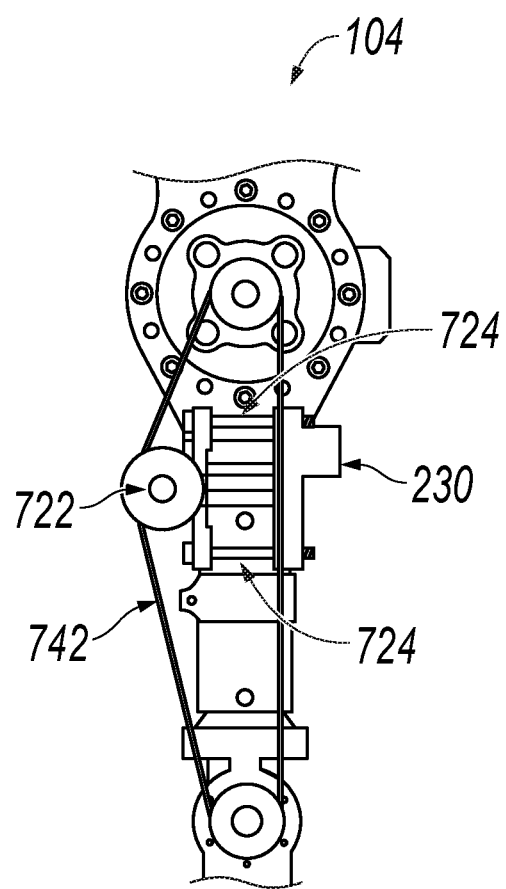
FIG. 7C illustrates an example of a tension pulley of FIG. 7A extended outward to increase tension on a belt.

FIG. 7C illustrates an example of the tension pulley 722 of FIG. 7A extended outward to increase tension on the belt 242. The first piece 718 is outwardly extended from the second piece 720 of the tensioner-mounting bracket 230 and is locked in place with the tensioner-locking devices 724 thereby increasing tension on the belt 242. As shown in FIG. 7A, the adjustable pylon 110 has coupled to the bottom end thereof, the upper hinge portion 234 of the surface-contacting portion 108. The surface-contacting portion 108 further includes the lower hinge portion 236 with the shaft 238 going through an opening of the upper hinge portion 234 and an opening of the lower hinge portion 236 thereby creating a hinge. The shaft 238 has coupled thereon the second pulley 240 in partial engagement with the belt 242. In various embodiments, the second pulley 240 can have a contacting surface that is operable to make at least partial contact with the belt 242. During operation, the ankle motor 220 transmits torque to the ankle joint via the first pulley 228, the belt 242, and the second pulley 240 sufficient to cause flexion and extension of the modular foot element 112 in a sagittal plane (i.e., an anterior-posterior plane) of the user.

Figure 8:
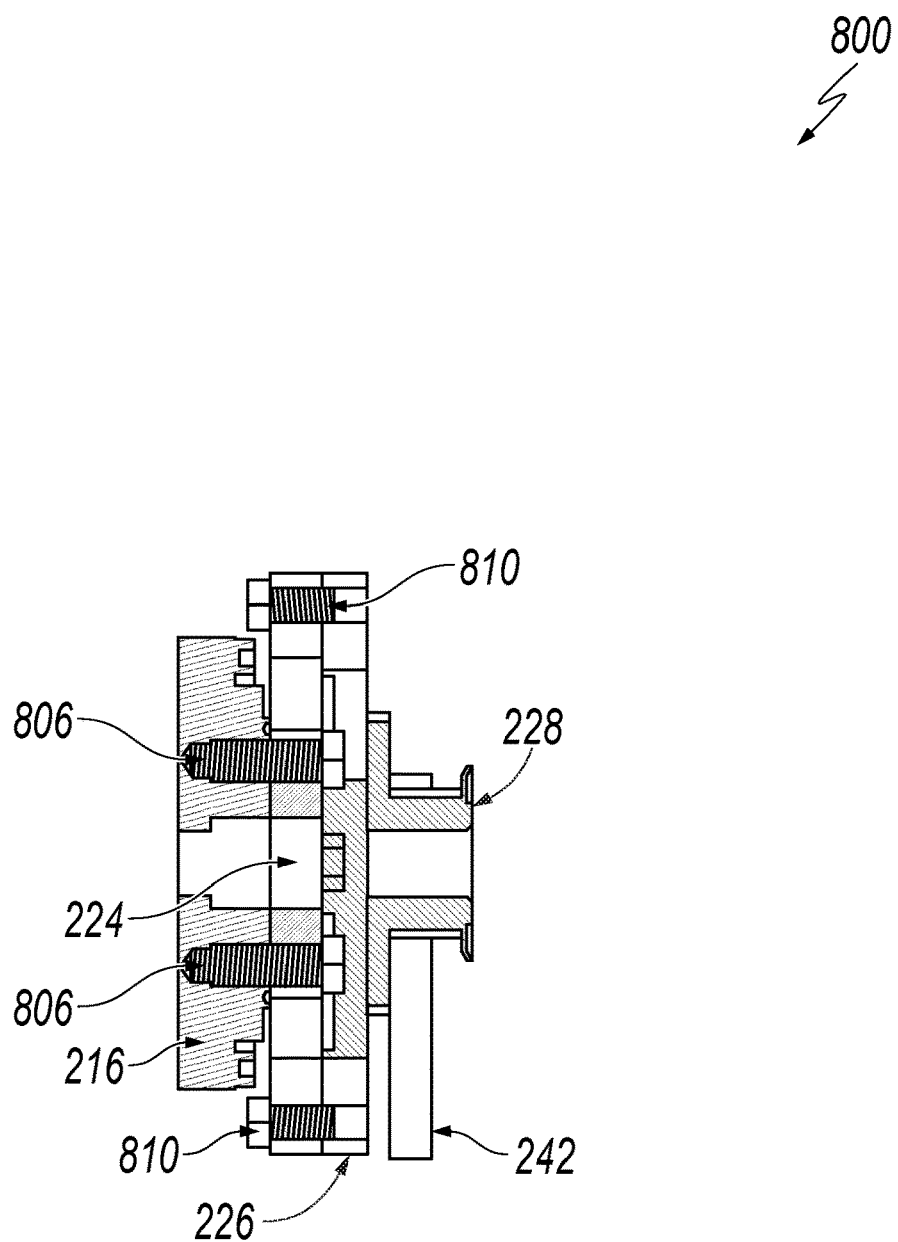
FIG. 8 illustrates a cross sectional view of an RSEA assembly according to an embodiment of the present disclosure.

FIG. 8 illustrates a cross sectional view of an RSEA assembly 800 according to an embodiment of the present disclosure. The RSEA assembly 800 includes the ankle harmonic drive 222 coupled to the RSEA 224 via harmonic drive connections 806. The RSEA 224 is coupled to the connecting disk 226 opposite the ankle harmonic drive 222 via connecting disk connections 810. The connecting disk 226, in turn, has coupled thereon the first pulley 228 that is at least partially engaged with the belt 242. In some embodiments, the harmonic drive connections 806 and the connecting disk connections 810 can be, for example, screws, setscrews, lock pins, nuts and bolts, clamps, clasps, and combinations of the same and like. In various embodiments, the first pulley 228 can have a contacting surface that is operable to make at least partial contact with the belt 242. During operation, elastic properties of the RSEA 224 enable the RSEA 224 to store torque produced by the ankle motor 220. Thus, the RSEA 224 is able to store torque for use during periods of peak torque requirements thereby reducing the torque demand on the ankle motor 220.

Figure 9:
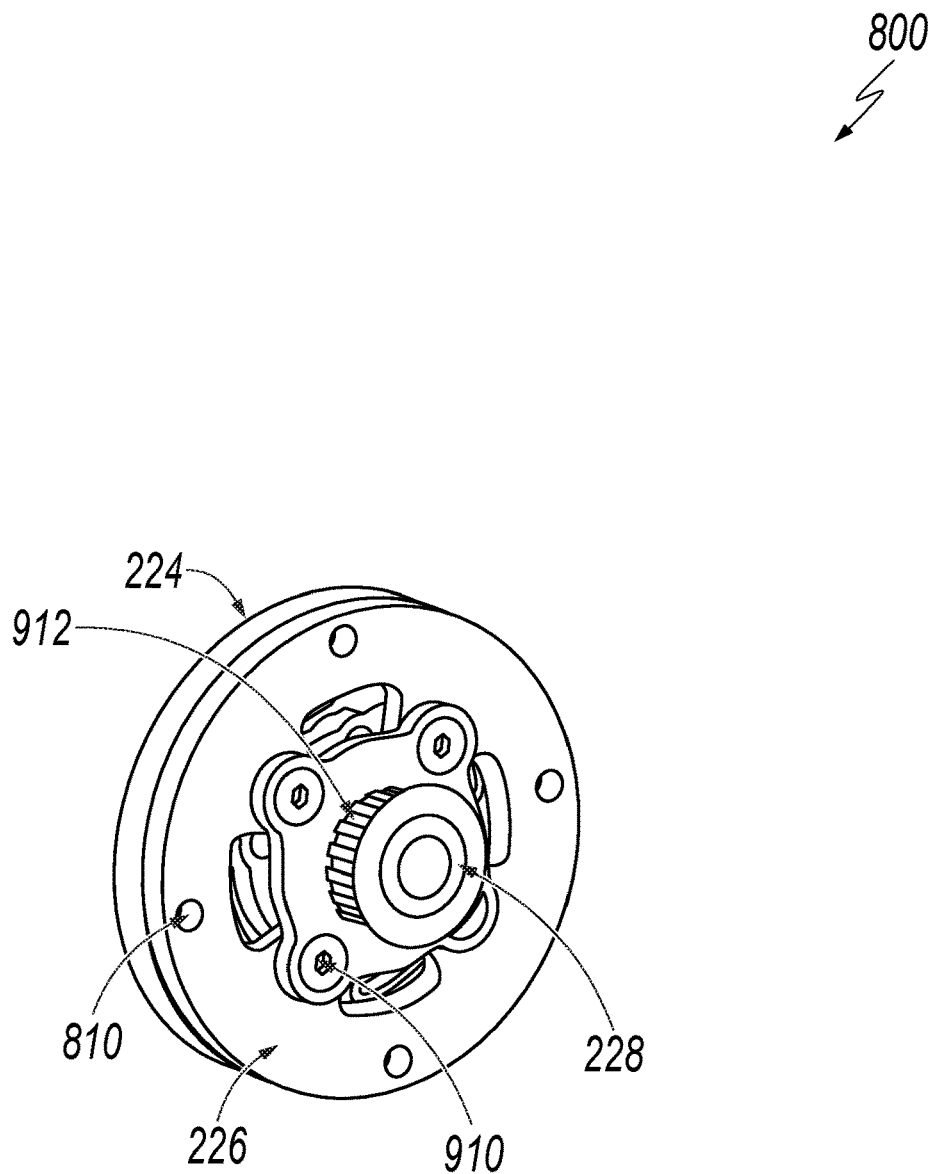
FIG. 9 illustrates a perspective view of the RSEA assembly according to an embodiment of the present disclosure.

FIG. 9 illustrates a perspective view of the RSEA assembly 800 according to an embodiment of the present disclosure. As shown in FIG. 9, the RSEA assembly 800 includes the RSEA 224 coupled to the connecting disk 226 via the connecting disk connections 810. The connecting disk 226 has the first pulley 228 connected thereon via pulley connections 910. The first pulley 228 includes a first contacting surface 912 for at least partial engagement of a belt, for example, the belt 242 of FIG. 2. In some embodiments, the pulley connections 910 can be, for example, screws, setscrews, lock pins, nuts and bolts, clamps, clasps, and combinations of the same and like.

Figure 10:
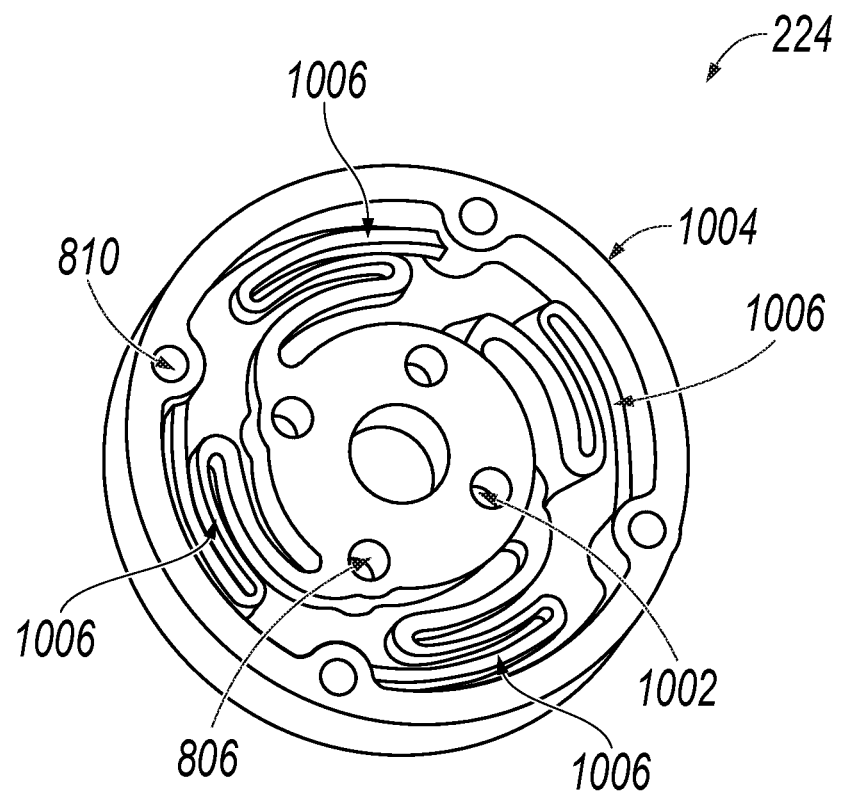
FIG. 10 illustrates a perspective view of the RSEA according to an embodiment of the present disclosure.

FIG. 10 illustrates a perspective view of the RSEA 224 according to an embodiment of the present disclosure. The RSEA 224 includes a circular inner portion 1002 coupled to a circular outer portion 1004 via sections of looping 1006. The circular inner portion 1002 includes openings of the harmonic drive connections 806 operable to couple to the ankle harmonic drive 222. Similarly, the circular outer portion 1004 includes openings of the connecting disk connections 810 operable to couple to the connecting disk 226. In various embodiments, the sections of looping 1006 can be formed with one loop, two loops (shown), three loops, four loops, or five or more loops. In a particular embodiment, each of the sections of looping 1006 of the RSEA 224 includes four loops. In some embodiments, the RSEA 224 can be composed of plastics, metals, metal-alloys, aluminum, carbon-fiber composites, steel, steel-alloys, and combinations of the same and like. During operation, elastic properties of the RSEA 224 enable the RSEA 224 to store torque produced by the ankle motor 220. Thus, the RSEA 224 is able to store torque for use during periods of peak torque requirements thereby reducing the torque demand on the ankle motor 220. In some embodiments, bending the RSEA 224 clockwise stresses the RSEA 224 less than bending it counterclockwise. As such, in these embodiments, the looping 1006 bends in a single direction. As such, the looping 1006 can survive larger deflections, thus potentially giving larger deflection before failure than typical RSEA springs with symmetric looping. In various embodiments, the RSEA 224 can be optimized to maximize one-directional deflection that will reduce the power requirements of the ankle motor 220.

Figure 11:
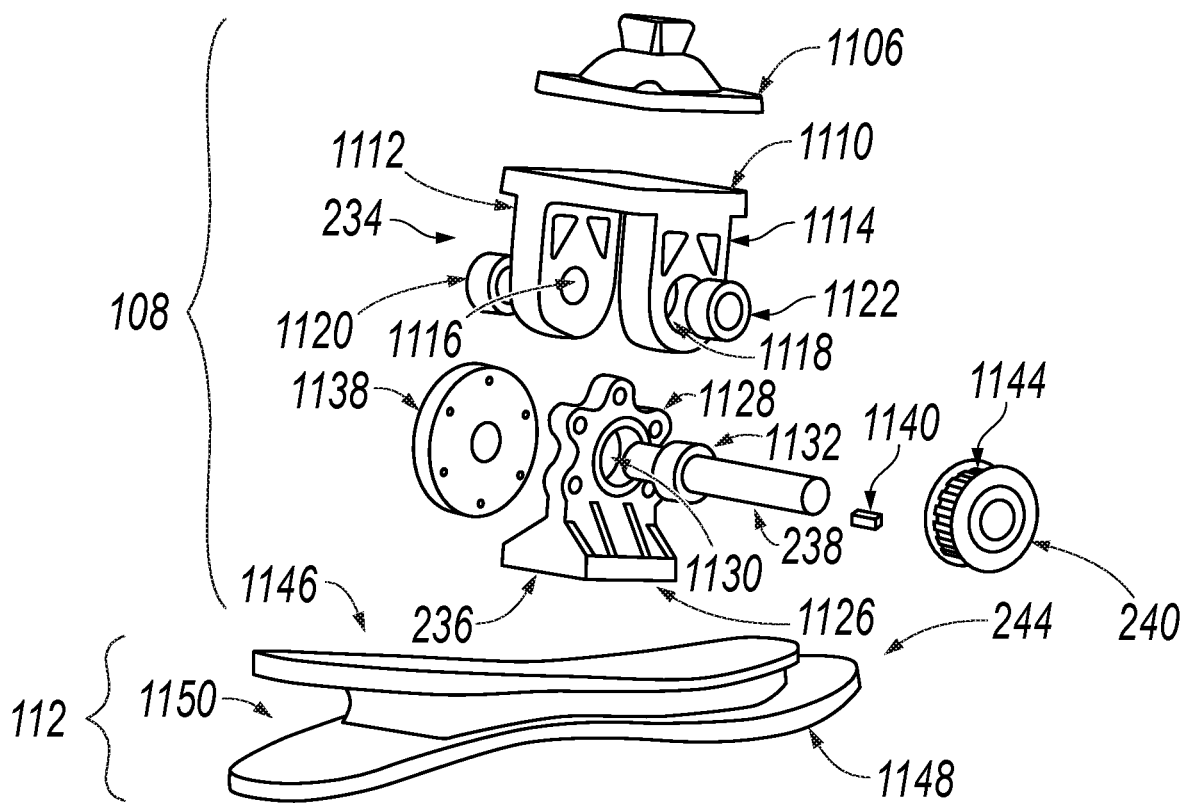
FIG. 11 illustrates an exploded view of a surface-contacting portion and a modular foot element according to an embodiment of the present disclosure.

FIG. 11 illustrates an exploded view of the surface-contacting portion 108 and the modular foot element 112 according to an embodiment of the present disclosure. The surface-contacting portion 108 includes a coupling device 1106 that is operable to be coupled to a lower end of the drive portion 106 and/or a bottom end of the adjustable pylon 110. The coupling device 1106 has the upper hinge portion 234 attached to an opposite end thereof. The upper hinge portion 234 includes an upper base 1110 with a first flange 1112 and a second flange 1114 extending downwardly perpendicular from the upper base 1110. The first flange 1112 has a first cavity 1116 and the second flange 1114 has a second cavity 1118. Each of the cavities 1116 and 1118 are operable to receive a first insert 1120 and a second insert 1122, respectively. As shown in FIG. 11, the surface-contacting portion 108 further includes the lower hinge portion 236 having a lower base 1126 with a third flange 1128 extending upwardly perpendicular from the lower base 1126. The third flange 1128 has a hole 1130 operable to receive a third insert 1132 and the shaft 238 therein. In some embodiments, as shown in FIG. 11, the shaft 238 can be a keyed shaft. The shaft 238 goes through the second insert 1122 in the second cavity 1118, the third insert 1132 in the hole 1130, and the first insert 1120 in the first cavity 1116 of the lower hinge portion 236 to thereby couple to a keyed flange 1138. The shaft 238 is locked into the keyed flange 1138 via a key 1140.

As shown in FIG. 11, the shaft 238 has the second pulley 240 connected opposite the keyed flange 1138. The second pulley 240 includes a second contacting surface 1144 for at least partial engagement of a belt, for example, the belt 242 of FIG. 2. As shown in FIG. 11, the lower hinge portion 236 couples to an upper foot portion 1146 of the flexible foot 244 that is a part of the modular foot element 112 via the lower base 1126. The upper foot portion 1146 is coupled to a lower foot portion 1148 and creates a wedge-shaped opening 1150 between the upper foot portion 1146 and the lower foot portion 1148 of the flexible foot 244. In some embodiments, the coupling device 1106, the first flange 1112, the second flange 1114, the third flange 1128, the keyed flange 1138, and the key 1140, can be constructed of, for example, plastics, metals, metal-alloys, aluminum, carbon-fiber composites, steel, steel-alloys, and combinations of the same and like. In various embodiments, the upper foot portion 1146 and the lower foot portion 1148 can be custom designed for walking, running, sporting activities, and the like, similar to the flexible foot 244 of FIG. 2. In some embodiments, the upper foot portion 1146 and the lower foot portion 1148 can be waterproof, similar to the flexible foot 244 of FIG. 2. In some embodiments, the upper foot portion 1146 and the lower foot portion 1148 can be constructed of, for example, plastics, metals, metal-alloys, aluminum, carbon-fiber composites, steel, steel-alloys, and combinations of the same and like. In some embodiments, the first insert 1120, the second insert 1122, and the third insert 1132 can each be general bearings, tensioner support bearings, adapters, washers, and combinations of the same and like.

In some embodiments, the surface-contacting portion 108 and/or the modular foot element 112 can further include sensors to measure force at a bottom end of the modular foot element 112. In various embodiments, the sensors can measure foot-contact reaction forces. In various embodiments, the surface-contacting portion 108 can further include sensors mounted on or inside various components of the surface-contacting portion 108 or mounted on a sensor-bracket attached to the surface-contacting portion 108. In these embodiments, the sensors can be encoders, inertial measurement unit sensors, force sensors, or other types of sensors that can monitor input/output information relating to angles between the powered prosthetic leg 100 and the modular foot element 112 or relative location/orientation of the powered prosthetic leg 100 and/or the modular foot element 112. In some embodiments, the sensors can measure specific forces or angular rates, and can use a combination of accelerometers and gyroscopes, similar to the sensors as described with respect to FIG. 2.

Figure 12:
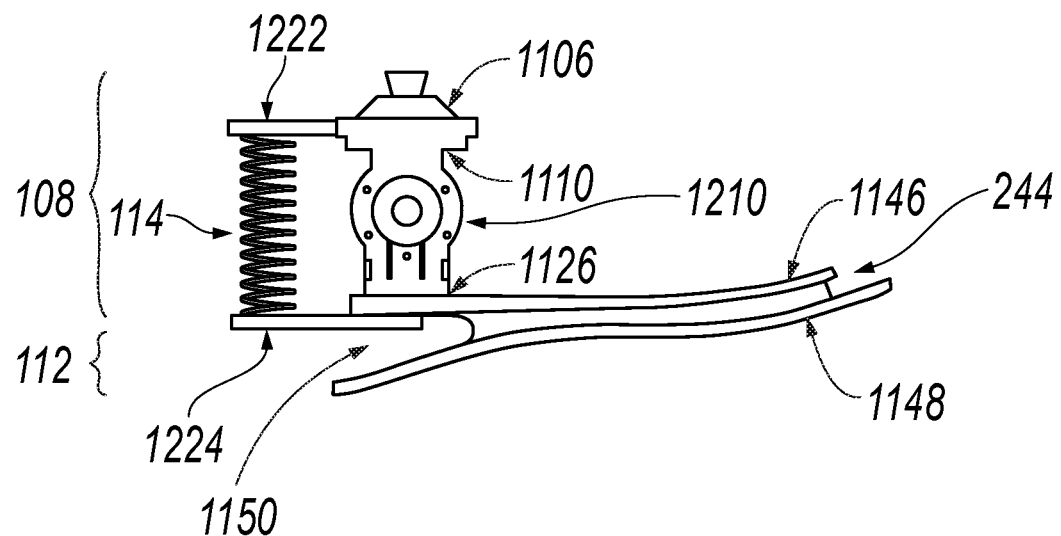
FIG. 12 illustrates the surface-contacting portion and the modular foot element utilizing a spring element according to an embodiment of the present disclosure.

FIG. 12 illustrates the surface-contacting portion 108 and the modular foot element 112 utilizing the spring element 114 according to an embodiment of the present disclosure. The surface-contacting portion 108 includes the coupling device 1106 that is operable to be coupled to a lower end of the drive portion 106 and/or a bottom end of the adjustable pylon 110. The coupling device 1106 couples to the hinge 1210 via the upper base 1110 of the hinge 1210. The hinge 1210 couples to a top portion of the upper foot portion 1146 of the modular foot element 112 via the lower base 1126 of the hinge 1210. The upper foot portion 1146 is coupled to the lower foot portion 1148 and creates the wedge-shaped opening 1150 between the upper foot portion 1146 and the lower foot portion 1148.

As shown in FIG. 12, a first support 1222 is coupled beneath the coupling device 1106 and above the upper base 1110 of the hinge 1210. The first support 1222 extends perpendicularly outward from the hinge 1210. A second support 1224 is coupled to a lower portion of the upper foot portion 1146 such that the second support 1224 is in the wedge-shaped opening 1150 extending perpendicularly outward from the hinge 1210. The spring element 114 is coupled between the first support 1222 and the second support 1224. In various embodiments, the spring element 1206 can be utilized to keep the upper foot portion 1146 and the lower foot portion 1148 that creates the flexible foot 244 in proper position and alignment. In some embodiments, the spring element 114 can be utilized to apply constant torque to the hinge 1210 and/or the RSEA 224 of FIG. 2. In some embodiments, the first support 1222 and the second support 1224 can be constructed of, for example, plastics, metals, metal-alloys, carbon-fiber composites, and combinations of the same and like.

In some embodiments, the spring element 1206 can be a compression spring, an extension spring, a torsional spring, a constant-force spring, a Belleville spring, pre-loaded springs, and combinations of the same and like. In some embodiments, elastic elements, such as springs, can be added between the upper foot portion 1146 and the lower foot portion 1148 at an end opposite the hinge 1210 to act as "toes" on the flexible foot 244 of the modular foot element 112. The elastic elements may include, for example, helical springs, elastic foam, compression elements, or other appropriate devices. In various embodiments, the elastic elements can be constructed of, for example, plastics, metals, metal-alloys, carbon-fiber composites, and combinations of the same and like. In various embodiments, the upper foot portion 1146 and the lower foot portion 1148 can extend outward and form the shape of a foot including separate extensions for each toe. Continuing this example, one or more toes formed by this configuration can have an elastic element between the upper foot portion 1146 and the lower foot portion 1148.

Figure 13:
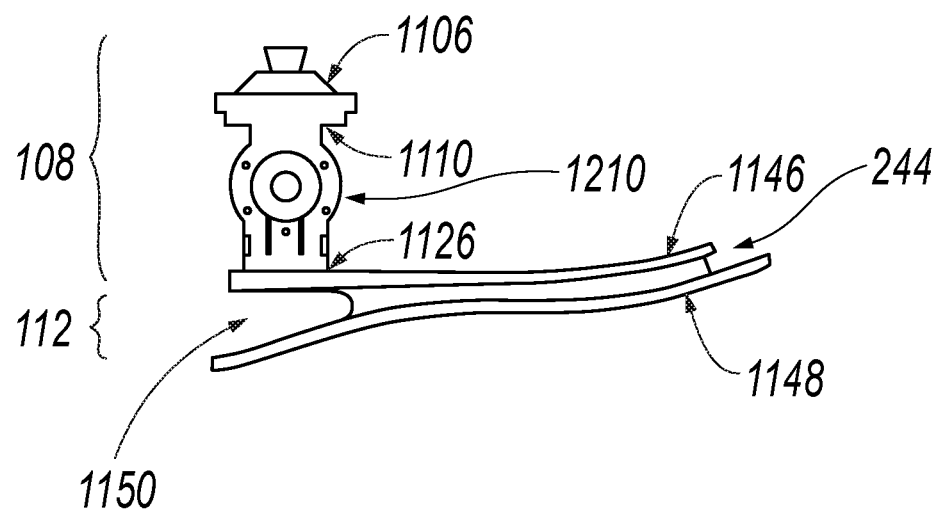
FIG. 13 illustrates the surface-contacting portion and the modular foot element omitting the spring element, according to an embodiment of the present disclosure.

FIG. 13 illustrates the surface-contacting portion 108 and the modular foot element 112 omitting the spring element 114, according to an embodiment of the present disclosure. The surface-contacting portion 108 includes the coupling device 1106 that is operable to be coupled to a lower end of the drive portion 106 and/or a bottom end of the adjustable pylon 110. The coupling device 1106 couples to a hinge 1210 via the upper base 1110 of the hinge 1210. The hinge 1210 couples to a top portion of the upper foot portion 1146 of the modular foot element 112 via the lower base 1126 of the hinge 1210. The upper foot portion 11460 is coupled to the lower foot portion 1148 and creates the wedge-shaped opening 1150 between the upper foot portion 1146 and the lower foot portion 1148 of the flexible foot 244. In some embodiments, elastic elements, such as springs, can be added between the upper foot portion 1146 and the lower foot portion 1148 at an end opposite the hinge 1210 to act as "toes" of the flexible foot 244 on the modular foot element 112. The elastic elements may include, for example, helical springs, elastic foam, compression elements, or other appropriate devices. In various embodiments, the elastic elements can be constructed of, for example, plastics, metals, metal-alloys, carbon-fiber composites, and combinations of the same and like. In various embodiments, the upper foot portion 1146 and the lower foot portion 1148 can extend outward and form the shape of a foot including separate extensions for each toe. Continuing this example, one or more toes formed by this configuration can have an elastic element between the upper foot portion 1146 and the lower foot portion 1148.

Figure 14:
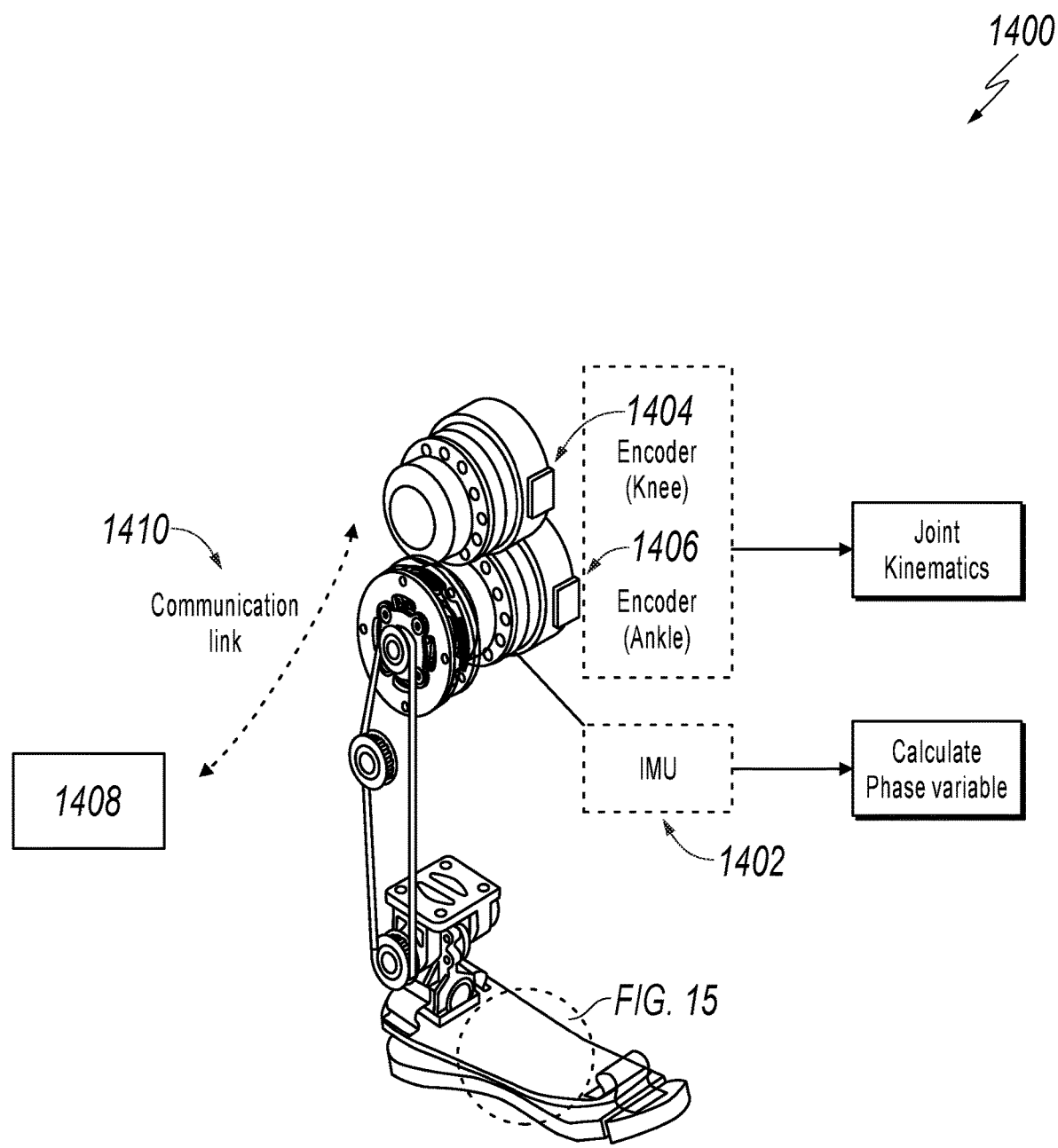
FIG. 14 is a block diagram of a control system for a powered prosthetic leg according to aspects of the present disclosure.

FIG. 14 illustrates a control system 1400 for the powered prosthetic leg 100 operable to communicate with various sensors. A first sensor 1402 is disposed proximate the knee joint of the powered prosthetic leg 100. In various embodiments, the first sensor 1402 can be, for example, an encoder, an inertial measurement unit, force sensors, or other types of sensor that can monitor input/output information relating to angles between the powered prosthetic leg 100 and, for example, the residual limb connected via the bracket 218 or relative location/orientation of the powered prosthetic leg 100. In some embodiments, the first sensor 1402 can measure specific forces or angular rates, and can use a combination of accelerometers and gyroscopes. In various embodiments, the first sensor 1402 is configured to measure angular displacement of the user's thigh in the sagittal plane about an axis of rotation extending through the user's hip joint in the coronal plane. In a particular embodiment, the first sensor 1402 is an inertial measurement unit.

A second sensor 1404 is disposed proximate the knee motor 216. In various embodiments, the second sensor 1404 can be an encoder, an inertial measurement unit, a force sensor, or other types of sensor that can monitor input/output information relating to angles between the powered prosthetic leg 100 and, for example, the residual limb connected via the bracket 218 or relative location/orientation of the powered prosthetic leg 100. In some embodiments, the sensors can measure specific forces or angular rates, and can use a combination of accelerometers and gyroscopes. In various embodiments, the at least one second sensor 1404 is configured to measure angular displacement of the knee joint in the sagittal plane (i.e., flexion and extension of the knee joint). In a particular embodiment, the second sensor 1404 is a knee encoder.

A third sensor 1406 is disposed proximate the ankle motor 220. In various embodiments, the third sensor 1406 can be an encoder, an inertial measurement unit, a force sensor, or other types of sensor that can monitor input/output information relating to angles between the powered prosthetic leg 100 and, for example, the residual limb connected via the bracket 218 or relative location/orientation of the powered prosthetic leg 100. In some embodiments, the sensors can measure specific forces or angular rates, and can use a combination of accelerometers and gyroscopes. In various embodiments, the third sensor 1406 is configured to measure angular displacement of the knee joint in the sagittal plane (i.e., flexion and extension of the knee joint). In a particular embodiment, the third sensor 1406 is an ankle encoder.

As will be discussed in further detail below, foot sensors can be disposed on and/or in the modular foot element 112 and can be configured to measure force at a bottom end of the modular foot element 112. In various embodiments, the foor sensors can measure foot-contact reaction forces. In such embodiments, the foot sensors are configured to measure contact force between the foot element 112 and the surface. In some embodiments, the foot sensors on the modular foot element 112 can be force sensors.

Still referring to FIG. 14, the first sensor 1402, the second sensor 1404, and the third sensor 1406 communicate with a control unit 1408 via a communications link 1410. In various embodiments, the control unit 1408 may be, for example, a motor control unit, a proportional, integral, derivative ("PID") controller, or any other type of controller. In various embodiments, the first sensor 1402, the second sensor 1404, and the third sensor 1406 communicate with the control unit via the communications link 1410 that can be, for example, a wired connection; however, in other embodiments, the first sensor 1402, the second sensor 1404, and the third sensor 1406 may communicate with the control unit 1408 via a wireless protocol operating over the communications link 1410. In various embodiments, the control unit 1408 is integral with the powered prosthetic leg 100; however, in other embodiments, the control unit may be worn remotely from the powered prosthetic leg 100 such as, for example, on a belt of the user. The control unit 1408 communicates with the knee motor 214 and the ankle motor 220. In various embodiments, the control unit 1408 communicates with the knee motor 214 and the ankle motor 220 via a wired connection over the communications link 1410; however, in other embodiments, the control unit 1408 communicates with the knee motor 214 and the ankle motor 220 via a wireless protocol operating over the communications link 1410.

During operation, the first sensor 1402, the second sensor 1404, and the third sensor 1406 provide signals to the control unit 1408 corresponding to, for example, relative location of the user's thigh and calf as well as contract force between the modular foot element 112 and the surface. The control unit 1408 signals the knee motor 214 and the ankle motor 220 to move in a manner sufficient to cause the powered prosthetic leg 100 to move in such a way as to facilitate, for example, walking. In various embodiments, the foot sensors located on the modular foot element 112 can communicate in the same manner with the control unit 1408 as the first sensor 1402, the second sensor 1404, or the third sensor 1406. The control system 1400 is described by way of example as including the first sensor, 1402, the second sensor 1404, and the third sensor 1406; however, in other embodiments, the control system 1400 may include any number of sensors positioned at various locations on the powered prosthetic leg 100.

Figure 15:
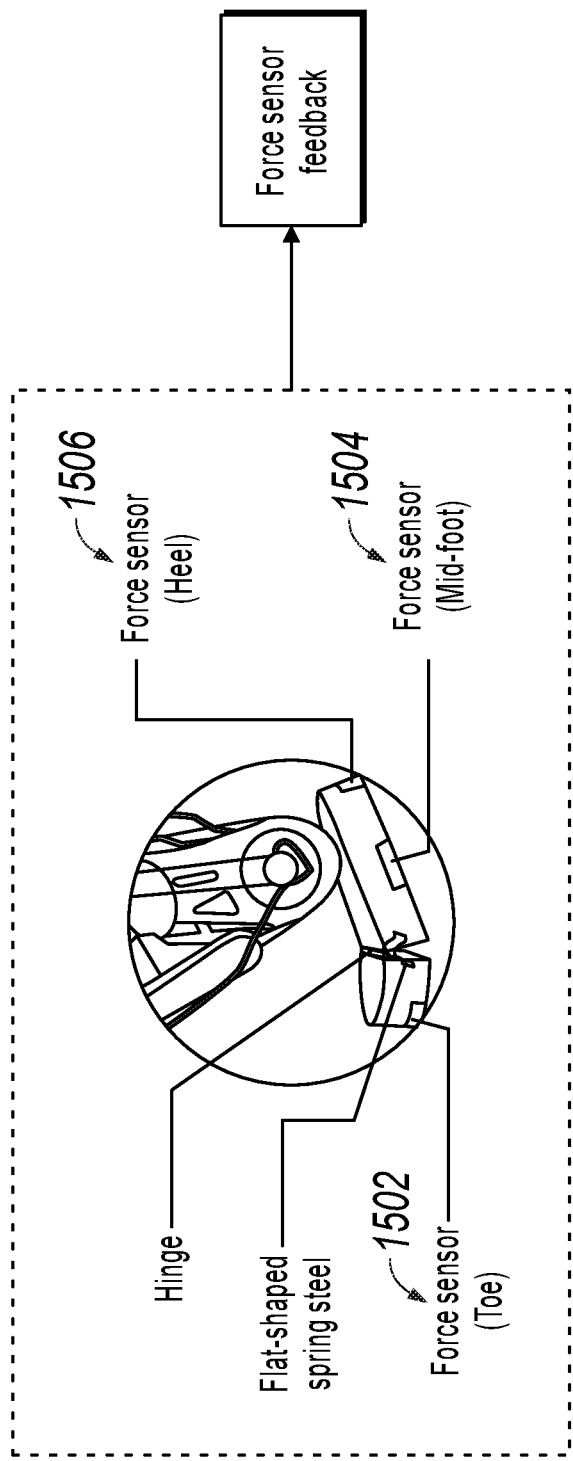
FIG. 15 illustrates the modular foot element with various foot sensors, for example, the foot sensors of FIG. 14.

FIG. 15 illustrates the modular foot element 112 with various foot sensors, for example, the foot sensors of FIG. 14. As shown in FIG. 15, the modular foot element 112 can include a toe force sensor 1502, a mid-foot force sensor 1504, and a heel force sensor 1506. In some embodiments, the toe force sensor 1502, the mid-foot force sensor 1504, and the heel force sensor 1506 can be configured to measure force at a bottom end of the modular foot element 112. In some embodiments, the toe force sensor 1502, the mid-foot force sensor 1504, and the heel force sensor 1506 can measure foot-contact reaction forces. In such embodiments, the toe force sensor 1502, the mid-foot force sensor 1504, and the heel force sensor 1506 are configured to measure contact force between the foot element 112 and the surface. The toe force sensor 1502, the mid-foot force sensor 1504, and the heel force sensor 1506 communicate with the control unit 1408 via the communications link 1410. In various embodiments, the toe force sensor 1502, the mid-foot force sensor 1504, and the heel force sensor 1506 communicate with the control unit 1408 via the communications link 1410 that can be, for example, a wired connection; however, in other embodiments, the toe force sensor 1502, the mid-foot force sensor 1504, and the heel force sensor 1506 may communicate with the control unit 1408 via a wireless protocol operating over the communications link 1410.

Figure 16:
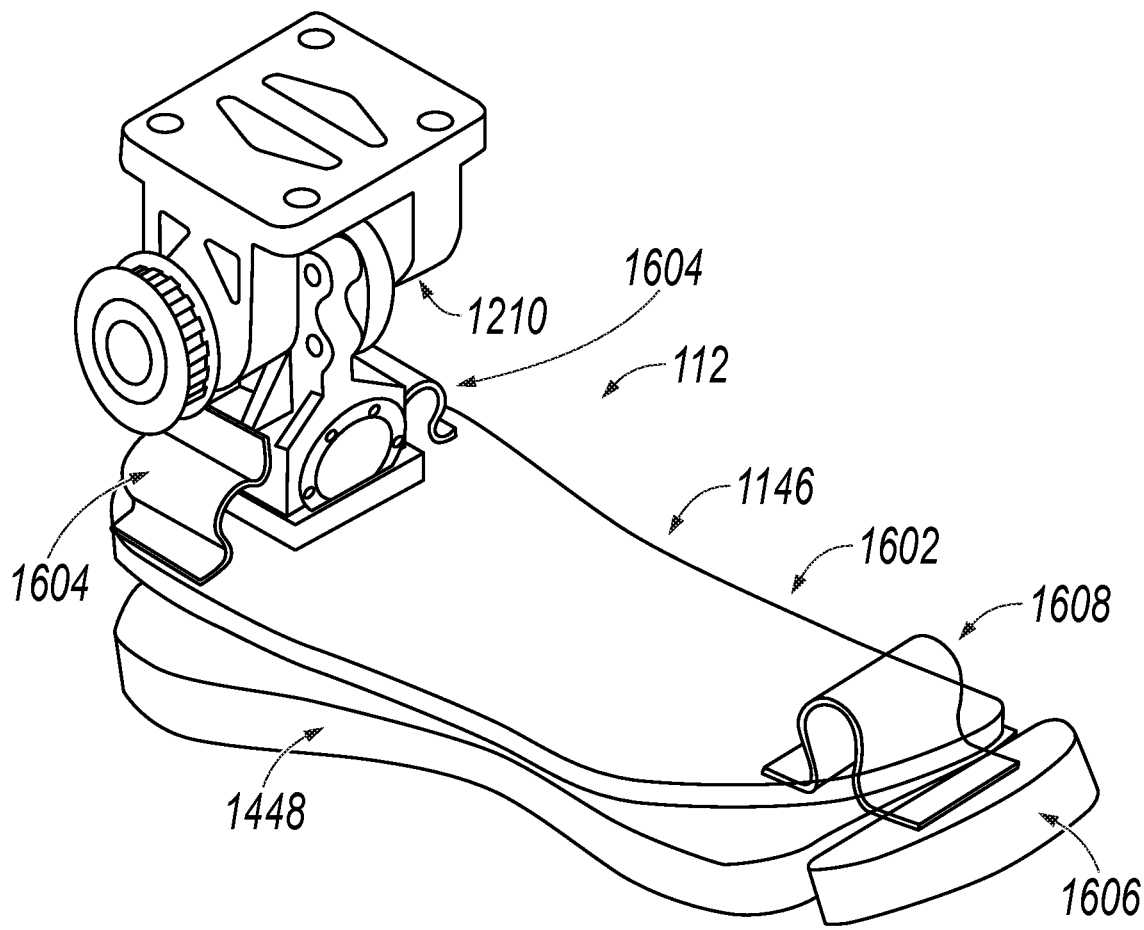
FIG. 16 illustrates an embodiment of the modular foot element 112 constructed of multiple components.

FIG. 16 illustrates an embodiment of the modular foot element 112 constructed of multiple components. As shown in FIG. 16, the hinge 1210 connects to a foot portion 1602 that includes the upper foot portion 1146 and the lower foot portion 1448. In some embodiments, the hinge 1210 can include foot brackets 1604 coupled to the upper foot portion 1146 of the foot portion 1602. The foot brackets 1604 can be constructed of, for example, plastics, metals, metal-alloys, carbon-fiber composites, and combinations of the same and like. In some embodiments, the foot brackets 1604 can be elastic. In various embodiments, the foot brackets 1604 are spring biased. The foot portion 1602 couples to a toe portion 1606 via a toe bracket 1608. The toe bracket 1608 can be constructed of, for example, plastics, metals, metal-alloys, carbon-fiber composites, and combinations of the same and like. In some embodiments, the toe bracket 1608 can be elastic. In various embodiments, the toe bracket 1608 is spring biased. In some embodiments, the toe portion 1606 can include the toe force sensor 1502. In various embodiments, the foot portion 1602 can include the mid-foot force sensor 1504 and the heel force sensor 1506.

Figure 17:
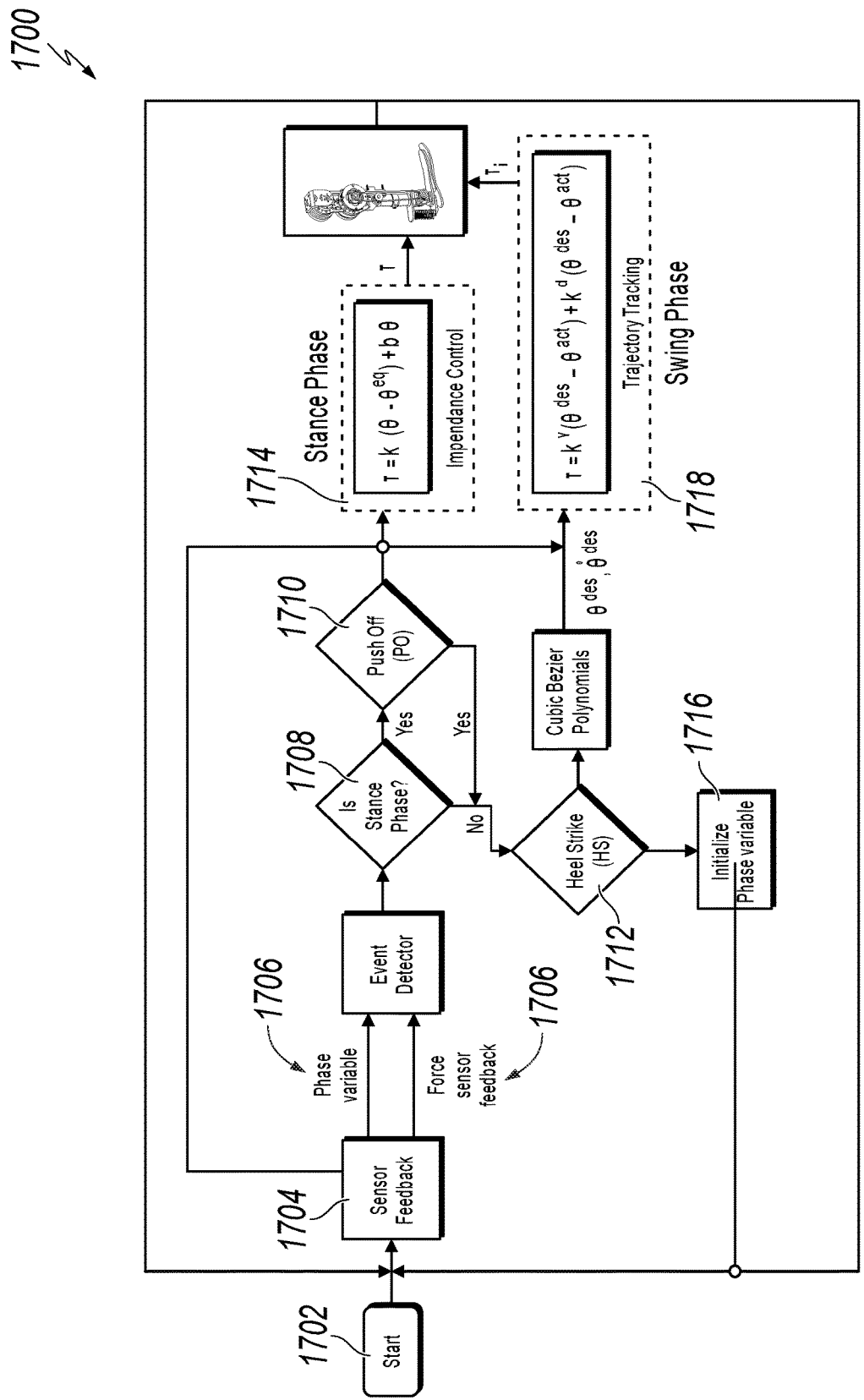
FIG. 17 is a flow diagram illustrating a control process for a powered prosthetic leg according to aspects of the invention.

FIG. 17 is a flow diagram illustrating a control process 1700 for a powered prosthetic leg 100. As used herein, the term "heel strike" refers to the moment that the heel of the powered prosthetic leg 100 makes contact with a surface during gait. The term "push off" refers to the moment that the toe portion of the powered prosthetic leg pushes against the surface to move the user's body forward until the toe portion leaves the ground. The term "stance phase" refers to the portion of the gait cycle where the powered prosthetic leg 100 is in contact with the surface. In various embodiments, stance phase begins at heel strike and ends at push off. The term "swing phase" refers to the portion of the gait cycle where the powered prosthetic leg 100 swings forward with no contact with the surface. In various embodiments, swing phase begins at push off and ends at heel strike.

Still referring to FIG. 17, the process 1700 begins at step 1702. At step 1704, the control unit 1408 receives feedback from a plurality of sensors associated with the powered prosthetic leg 100. In various embodiments the plurality of sensors may include, for example, the first sensor 1402, the second sensor 1404, and the third sensor 1406. In some embodiments, the plurality of sensors may include, for example, the toe force sensor 1502, the mid-foot force sensor 1504, and the heel force sensor 1506. At step 1706, the sensor feedback is provided to an event detector together with a phase variable. In various embodiments, the event detector is integral with the control unit 1408; however, in other embodiments, the event detector may be a stand-alone unit. In various embodiments, the phase variable is a time-independent variable that parameterizes the phases of the human gait cycle. The phase variable allows the event detector to determine the phase of the gait cycle. At step 1708, the event detector determines if the powered prosthetic leg 100 is in the stance phase. If, at step 1708, it is determined that the powered prosthetic leg 100 is in the stance phase, the process 1700 proceeds to step 1710. If, at step 1708, it is determined that the powered prosthetic leg 100 is not in the stance phase, the process 1700 proceeds to step 1712. At step 1710, the event detector determines if the powered prosthetic leg 100 has experienced push off. If at step 1710, it is determined that push off has occurred, the process 1700 proceed to step 1712. If, at step 1710, it is determined that push off has not occurred, the process proceeds to step 1714. At step 1714, the control unit 1408 provides impedance control to the knee motor 214 and the ankle motor 220 to affect the gait cycle of the powered prosthetic leg 100. From step 1714, the process 1700 returns to step 1704.

Still referring to FIG. 17, at step 1712, it is determined if the powered prosthetic leg has experienced heel strike. If, at step 1712, it is determined that heel strike has occurred, the process 1700 proceeds to step 1716 where the phase variable is initialized for a subsequent gait cycle. From step 1716, the process returns to step 1704. If, at step 1712, it is determined that heel strike has not occurred, the process 1700 proceeds to step 1718 where the control unit 1408 actuates the knee motor 214 and the ankle motor 220 to provide trajectory tracking for the powered prosthetic leg 100. In various embodiments, the trajectory tracking in step 1718 utilizes, for example, cubic Bezier polynomials to parameterize the desired trajectory of the powered prosthetic leg 100. From step 1718, the process 1700 returns to step 1704.

Although various embodiments of the present disclosure have been illustrated in the accompanying Drawings and described in the foregoing Detailed Description, it will be understood that the present disclosure is not limited to the embodiments disclosed herein, but is capable of numerous rearrangements, modifications, and substitutions without departing from the spirit of the disclosure as set forth herein.

The term "substantially" is defined as largely but not necessarily wholly what is specified, as understood by a person of ordinary skill in the art. In any disclosed embodiment, the terms "substantially," "approximately," "generally," and "about" may be substituted with "within [a percentage] of" what is specified, where the percentage includes 0.1, 1, 5, and 10 percent.

The foregoing outlines features of several embodiments so that those skilled in the art may better understand the aspects of the disclosure. Those skilled in the art should appreciate that they may readily use the disclosure as a basis for designing or modifying other processes and structures for carrying out the same purposes and/or achieving the same advantages of the embodiments introduced herein. Those skilled in the art should also realize that such equivalent constructions do not depart from the spirit and scope of the disclosure, and that they may make various changes, substitutions, and alterations herein without departing from the spirit and scope of the disclosure. The scope of the invention should be determined only by the language of the claims that follow. The term "comprising" within the claims is intended to mean "including at least" such that the recited listing of elements in a claim are an open group. The terms "a," "an," and other singular terms are intended to include the plural forms thereof unless specifically excluded.

What is claimed is:

1. A prosthetic leg comprising:
    a modular knee element coupled to a modular ankle element;
    the modular knee element comprising a knee motor, wherein the modular knee element is rotatable about an axis of a shaft in the knee motor;
    the modular ankle element comprising a drive portion coupled to a surface-contacting portion via a pylon that comprises a top end and a bottom end;
        wherein the top end of the pylon is coupled to the drive portion of the modular ankle element and the bottom end of the pylon is coupled to the surface-contacting portion of the modular ankle element;
    the drive portion of the modular ankle element comprising:
        an ankle motor coupled to a rotary series elastic actuator (RSEA); and
        a first pulley coupled to the RSEA;
    the surface-contacting portion of the modular ankle element comprising:
        a shaft and flange engaged in a hinge rotatable about an axis of the shaft and flange; and
        a second pulley coupled to the shaft and flange;
    a belt engaging at least a portion of at least one of the first pulley and the second pulley; and
    a modular foot element coupled to the bottom of the hinge.

2. The prosthetic leg of claim 1, wherein the modular knee element comprises:
    a bracket operable to connect to a residual limb; and
    a knee harmonic drive coupled to the knee motor.

3. The prosthetic leg of claim 1, wherein the pylon is an adjustable pylon.

4. The prosthetic leg of claim 1, wherein the drive portion of the modular ankle element comprises:
    an ankle harmonic drive coupled between the ankle motor and the RSEA;

a connecting disk coupled to the RSEA opposite the ankle harmonic drive, wherein the first pulley is coupled to the connecting disk; and a tensioner-mounting bracket coupled to a belt tensioner, wherein the belt engages at least a portion of the belt tensioner.

5. The prosthetic leg of claim 4, where the belt tensioner is adjustable to facilitate vertical adjustment of the pylon.

6. The prosthetic leg of claim 1, wherein the second pulley is between the bottom end of the pylon and a bottom of the surface-contacting portion of the modular ankle element.

7. The prosthetic leg of claim 1, wherein the surface-contacting portion of the modular ankle element comprises a spring element connected above the hinge and below the hinge.

8. The prosthetic leg of claim 1, wherein:
the modular foot element comprises at least one segmented portion defined by a spacing between a top portion of the modular foot element and a bottom portion of the modular foot element;
the at least one segmented portion is opposite the hinge; and
the at least one segmented portion comprises an elastic element between the top portion and the bottom portion.

9. The prosthetic leg of claim 1, wherein at least one of the knee motor and ankle motor are battery-powered.

10. The prosthetic leg of claim 1, wherein the prosthetic leg comprises at least one sensor.

11. The prosthetic leg of claim 10, wherein:
the at least one sensor is at least one of an encoder, an inertial measurement unit sensor, a force sensor, an accelerometer, and a gyroscope; and
the at least one sensor is coupled to at least one of the modular knee element, the modular ankle element, and the modular foot element.

12. The prosthetic leg of claim 1, wherein the modular foot element comprises a flexible foot.

13. The prosthetic leg of claim 1, wherein the RSEA is composed of at least one of plastics, metals, metal-alloys, aluminum, carbon-fiber composites, steel, and steel-alloys.

14. The prosthetic leg of claim 1, wherein elastic properties of the RSEA enable the RSEA to store torque generated by the ankle motor.

15. The prosthetic leg of claim 1, wherein the modular knee element, the modular ankle element, and the modular foot element are selectively interchangeable.

16. A powered prosthetic leg comprising:
a modular knee element coupled to a modular ankle element;
the modular knee element comprising:
a bracket operable to connect to a residual limb; and
a knee motor coupled to a knee harmonic drive;
wherein the modular knee element is rotatable about an axis of a shaft in the knee motor;
the modular ankle element comprising a drive portion coupled to a surface-contacting portion via an adjustable pylon comprising a top end and a bottom end, wherein the top end of the adjustable pylon is coupled to the drive portion of the modular ankle element and the bottom end of the adjustable pylon is coupled to the surface-contacting portion of the modular ankle element;
the drive portion of the modular ankle element comprising:
an ankle motor coupled to an ankle harmonic drive;
a rotary series elastic actuator (RSEA) coupled to the ankle harmonic drive;
a first pulley coupled to the RSEA; and
the surface-contacting portion of the modular ankle element comprising:
a shaft and flange engaged in a hinge rotatable about an axis of the shaft and flange;
a spring element connected above the hinge and below the hinge; and
a second pulley coupled to the shaft and flange;
a belt engaging at least a portion of at least one of the first pulley and the second pulley; and
a modular foot element coupled to the bottom of the hinge.

17. The powered prosthetic leg of claim 16, wherein elastic properties of the RSEA enable the RSEA to store torque generated by the ankle motor.

18. The powered prosthetic leg of claim 16, wherein the modular knee element, the modular ankle element, and the modular foot element are selectively interchangeable.

* * * * *